(12) United States Patent
Donoho et al.

(10) Patent No.: US 6,720,412 B2
(45) Date of Patent: Apr. 13, 2004

(54) HUMAN THROMBOSPONDIN REPEAT PROTEINS AND POLYNUCLEOTIDES ENCODING THE SAME

(75) Inventors: Gregory Donoho, The Woodlands, TX (US); John Scoville, Houston, TX (US); C. Alexander Turner, Jr., The Woodlands, TX (US); Glenn Friedrich, Houston, TX (US); Brian Zambrowicz, The Woodlands, TX (US); Arthur T. Sands, The Woodlands, TX (US)

(73) Assignee: Lexicon Genetics Corporation, The Woodlands, TX (US)

(*) Notice: Subject to any disclaimer, the term of this patent is extended or adjusted under 35 U.S.C. 154(b) by 0 days.

(21) Appl. No.: 09/784,358

(22) Filed: Feb. 15, 2001

(65) Prior Publication Data

US 2002/0099027 A1 Jul. 25, 2002

Related U.S. Application Data

(60) Provisional application No. 60/183,282, filed on Feb. 17, 2000.

(51) Int. Cl.[7] ............................................. C07H 21/04
(52) U.S. Cl. ................................................... 536/23.2
(58) Field of Search ....................... 530/350; 536/23.1, 536/23.2; 435/69.1

(56) References Cited

U.S. PATENT DOCUMENTS

| | | |
|---|---|---|
| 4,215,051 A | 7/1980 | Schroeder et al. |
| 4,376,110 A | 3/1983 | David et al. |
| 4,594,595 A | 6/1986 | Struckman |
| 4,631,211 A | 12/1986 | Houghten |
| 4,689,405 A | 8/1987 | Frank et al. |
| 4,713,325 A | 12/1987 | Lutz |
| 4,946,776 A | 8/1990 | Ritterband |
| 5,252,743 A | 10/1993 | Barrett et al. |
| 5,424,186 A | 6/1995 | Fodor et al. |
| 5,445,934 A | 8/1995 | Fodor et al. |
| 5,459,127 A | 10/1995 | Felgner et al. |
| 5,556,752 A | 9/1996 | Lockhart et al. |
| 5,700,637 A | 12/1997 | Southern |
| 5,744,305 A | 4/1998 | Fodor et al. |
| 5,869,336 A | 2/1999 | Meyer et al. |
| 5,877,397 A | 3/1999 | Lonberg et al. |
| 5,948,767 A | 9/1999 | Scheule et al. |
| 6,075,181 A | 6/2000 | Kucherlapati et al. |
| 6,110,490 A | 8/2000 | Thierry |
| 6,150,584 A | 11/2000 | Kucherlapati et al. |
| 2003/0059768 A1 * | 3/2003 | Vernet et al. |

FOREIGN PATENT DOCUMENTS

| | | | |
|---|---|---|---|
| WO | WO 94 13794 A | 6/1994 | |

OTHER PUBLICATIONS

Mahairas et al. Sequence–tagged connectors: a sequence approach to mapping and scanning the human genome. Proc Natl Acad Sci U S A. Aug. 17, 1999; 96(17):9739–44.*

Bonaldo MF, Lennon G, Soares MB. Normalization and subtraction: two approaches to facilitate gene discovery. Genome Res Sep. 1996; 6(9):791–806. (Abstract).*

Database EM_HUM Online! EMBL; Nov. 11, 1999, Ohara et al, "Homo sapiens mRNA for KIAA1233 protein, partial cds" retreived from EBI, accession No. AB033059, XP002176788.

Database Swall Online!May 1, 2000, Nagase et al.: "KIAA1233 Protein (Fragment)" retrieved from EBI, accession No. Q9UL17, XP002176789.

Nagase et al. Prediction of the coding sequences of unidentified human genes XV The complete sequences of 100 new cDNA clones from brain which code for large proteins in vitro: DNA Researh. vol 6, 1999, pp. 337–345, XP000865804, gene No. KIAA1233.

Database EM_EST "Online!EMBL: Jan. 5, 1988, Hillier et al.: zj33e01 s1 Soares_fetal_liver_spleen_1NFLS_S1 Homo sapiens cDNA clone Image: 452088 3'similar to TR: P97857 P97857 Secretory Protein Containing Thrombospondin Motifs., MRNA sequence" retrieved from EBI, accession No. AA707140, XP002176790.

International Search Report, International Application No. PCT/US01/05290.

Bird et al, 1988, "Single–Chain Antigen–Binding Proteins", Science 242:423–426.

Bitter et al, 1987, "Expression and Secretion Vectors for Yeast", Methods in Enzymology 153:516–544.

Colbere–Garapin et al, 1981, "A New Dominant Hybrid Selective Marker for Higher Eukaryotic Cells", 150:1–14.

Gautier et al, 1987, "a–DNA IV: α–anomeric and β–anomeric tetrahymidylates covalently linked to intercalating oxazolopyridocarbazole. Synthesis, physiochemical properties and poly (rA) binding", Nucleic Acids Research 15(16):6625–6641.

Greenspan et al, 1993, "Idiotypes: structure and immunogenicity", FASEB Journal 7:437–444.

Huse et al, 1989, "Generation of a Large Combinatorial Library of the Immunoglobulin Reperoire in Phage Lambda", Science 246:1275–1281.

Huston et al, 1988, "Protein engineering of antibody binding sites: recovery of specific activity in an anti–digoxin single–chain Fv analogue produced in *Escherichia coli*", Proc. Natl. Acad. Sci. USA 85:5879–5883.

Inoue et al. 1987, "Sequence–dependent hydrolysis of RNA using modified oligonucleotide splints and R Nase H", FEBS Letters 215(2):327–330.

(List continued on next page.)

*Primary Examiner*—Karen Cochran Carlson
*Assistant Examiner*—Sheridan K Snedden

(57) ABSTRACT

Novel human polynucleotide and polypeptide sequences are disclosed that can be used in therapeutic, diagnostic, and pharmacogenomic applications.

5 Claims, No Drawings

OTHER PUBLICATIONS

Inoue et al, 1987, "Synthesis and hybridization studies on two complementary nona92'–O–methy)ribonucleotides", Nucleic Acids Research 15(15):6131–6149.

Inouye & Inouye, 1985, "Up–promoter mutations in the lpp gene of *Escherichia coli*", Nucleic Acids Research 13(9):3101–3110.

Janknecht et al. 1991, "Rapid and efficient purification of native histidine–tagged protein expressed by recombinant vaccinia virus", PNAS 88:8972–8976.

Kohler & Milstein, 1975, "Continuous cultures of fused cells secreting antibody of predefinced specificity", Nature 256:495–497.

Logan et al, 1984, "Adenovirus triparite leader sequence enhances translation of mRNAs late after infection", Proc. Natl. Acad. Sci. USA 81:3655–3659.

Lowry et al, 1980, "Isolation of Transforming DNA: Cloning the Hamster aprt Gene", Cell 22:817–823.

Morrison et al, 1994, "Chimeric human antibody molecules: Mouse antigen–binding domains with human constant region domains", Proc. Natl. Acad. Sci. 81:6851–6855.

Mulligan & Berg, 1981, "Selection of animal cells that express the *Escherichia coli* gene coding for xanthine–guanine phosphoribosyltransferase", Proc. Natl. Acad. Sci. USA 78(4):2072–2076.

Nisonoff, 1991, "Idiotypes: Concept and Applications", J. of Immunology 147:2429–2438.

O'Hare et al, 1981, "Transformation of mouse fibroblasts to methotrexate resistance by a recombinant plasmid expressing a prokaryotic dihydrofolate reductase", Proc. Natl. Acad. Sci. USA 78(3):1527–1531.

Santerre et al, 1984, "Expression of prokaryotic genes for hygromycin B and G418 resistance ans dominant–selection markers in mouse L cells", Gene 30:147–156.

Sarin et al, 1988, "Inhibition of acquired immunedeficiency syndrome virus by oligodeoxynucleoside methylphosphonates", Proc. Natl. Acad. Sci. USA 85:7448–7451.

Smith et al, 1983, "Molecular Engineering of the Autographa california Nuclear Polyhedrosis Virus Genome: Deletion Mutations within the Polyhedrin Gene", J. Virol. 46(2):584–593.

Stein, et al, 1988, "Physiochemical properties of phosphorothioate oligodeoxynucleotides", Nucleic Acids Research 16(8):3209–3221.

Szybalska & Szybalski, 1962, "Genetics of Human Cell Lines. IV. DNa–Mediated Heritable Transformation of a Biochemical Trait", Proc. Natl. Acad. Sci. USA 48:2026–2034.

Takeda et al, 1995, "Construction of chimaeric processed immunoglobulin genes containing mouse variable and human constant region sequences", Nature 314:452–454.

Van Heeke et al, 1989, "Expression of Human Asparagins Synthetase in *Escherichia coli* ", J. Biol. Chemistry 264(10):5503–5509.

Ward et al. 1989, "Binding activities of a repertoire of single immunoglobulin variable domains secreted from *Escherichia coli*", Nature 341:544–546.

Wigler et al, 1977, "Transfer of Purified Herpes Virus Thymidine Kinase Gene to Cultured Mouse Cells", Cell 11:223–232.

Wigler et al, 1980, "Transformation of mammalian cells with an amplifiable dominant–acting gene", Proc. Natl. Acad. Sci. USA 77(6):3567–3570.

* cited by examiner

HUMAN THROMBOSPONDIN REPEAT PROTEINS AND POLYNUCLEOTIDES ENCODING THE SAME

The present application claims the benefit of U.S. Provisional Application No. 60/183,282 which was filed on Feb. 17, 2000 and is herein incorporated by reference in its entirety.

1. INTRODUCTION

The present invention relates to the discovery, identification, and characterization of novel human polynucleotides encoding proteins that share sequence similarity with animal proteins having thrombospondin repeats. The invention encompasses the described polynucleotides, host cell expression systems, the encoded proteins, fusion proteins, polypeptides and peptides, antibodies to the encoded proteins and peptides, and genetically engineered animals that either lack or over express the disclosed polynucleotide sequences, antagonists and agonists of the proteins, and other compounds that modulate the expression or activity of the proteins encoded by the disclosed polynucleotide sequences that can be used for diagnosis, drug screening, clinical trial monitoring, the treatment of diseases and disorders, or cosmetic or nutriceutical applications.

2. BACKGROUND OF THE INVENTION

Thrombospondins have been implicated in, inter alia, mediating angiogensis, cancer, and development. Proteins having thrombospondin repeats can act as receptors, secreted extracellular matrix proteins, and proteases.

3. SUMMARY OF THE INVENTION

The present invention relates to the discovery, identification, and characterization of nucleotides that encode novel human proteins, and the corresponding amino acid sequences of these proteins. The novel human proteins (NHPs) described for the first time herein share structural similarity with proteins having thrombospondin repeats.

The novel human nucleic acid sequences described herein, encode alternative proteins/open reading frames (ORFs) of 1,691, 446, 372, 724, 650, 845, 771, and 1,617 amino acids in length (see SEQ ID NOS: 2, 4, 6, 8, 10, 12, 14, and 16 respectively).

The invention also encompasses agonists and antagonists of the described NHPs, including small molecules, large molecules, mutant NHPs, or portions thereof that compete with native NHP, peptides, and antibodies, as well as nucleotide sequences that can be used to inhibit the expression of the described NHPs (e.g., antisense and ribozyme molecules, and gene or regulatory sequence replacement constructs) or to enhance the expression of the described NHP polynucleotide sequences (e.g., expression constructs that place the described polynucleotide sequence under the control of a strong promoter system), and transgenic animals that express a NHP transgene, or "knockouts" (which can be conditional) that do not express a functional NHP.

Further, the present invention also relates to processes for identifying compounds that modulate, i.e., act as agonists or antagonists, of NHP expression and/or NHP activity that utilize purified preparations of the described NHPs and/or NHP product, or cells expressing the same. Such compounds can be used as therapeutic agents for the treatment of any of a wide variety of symptoms associated with biological disorders or imbalances.

4. DESCRIPTION OF THE SEQUENCE LISTING AND FIGURES

The Sequence Listing provides the sequences of the described NHP ORFs that encode the described NHP amino acid sequences. SEQ ID NO:17 describes a NHP ORF and flanking regions.

5. DETAILED DESCRIPTION OF THE INVENTION

The NHPs, described for the first time herein, are novel proteins that are expressed in, inter alia, human cell lines, human pituitary, lymph node, prostate, testis, adrenal gland, uterus, fetal kidney, fetal lung, and gene trapped human cells.

The present invention encompasses the nucleotides presented in the Sequence Listing, host cells expressing such nucleotides, the expression products of such nucleotides, and: (a) nucleotides that encode mammalian homologs of the described polynucleotide sequences, including the specifically described NHPs, and the NHP products; (b) nucleotides that encode one or more portions of the NHPs that correspond to functional domains, and the polypeptide products specified by such nucleotide sequences, including but not limited to the novel regions of any active domain(s); (c) isolated nucleotides that encode mutant versions, engineered or naturally occurring, of the described NHPs in which all or a part of at least one domain is deleted or altered, and the polypeptide products specified by such nucleotide sequences, including but not limited to soluble proteins and peptides in which all or a portion of the signal sequence is deleted; (d) nucleotides that encode chimeric fusion proteins containing all or a portion of a coding region of a NHP, or one of its domains (e.g., a receptor or ligand binding domain, accessory protein/self-association domain, etc.) fused to another peptide or polypeptide; or (e) therapeutic or diagnostic derivatives of the described polynucleotides such as oligonucleotides, antisense polynucleotides, ribozymes, dsRNA, or gene therapy constructs comprising a sequence first disclosed in the Sequence Listing.

As discussed above, the present invention includes:
(a) the human DNA sequences presented in the Sequence Listing (and vectors comprising the same) and additionally contemplates any nucleotide sequence encoding a contiguous NHP open reading frame (ORF) that hybridizes to a complement of a DNA sequence presented in the Sequence Listing under highly stringent conditions, e.g., hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3) and encodes a functionally equivalent gene product. Additionally contemplated are any nucleotide sequences that hybridize to the complement of a DNA sequence that encodes and expresses an amino acid sequence presented in the Sequence Listing under moderately stringent conditions, e.g., washing in 0.2×SSC/0.1% SDS at 42° C. (Ausubel et al., 1989, supra), yet still encodes a functionally equivalent NHP product. Functional equivalents of a NHP include naturally occurring NHPs present in other species and mutant NHPs whether naturally occurring or engineered (by site directed mutagenesis, gene shuffling, directed evolution as described in, for example, U.S. Pat. No. 5,837,458). The invention also includes degenerate nucleic acid variants of the disclosed NHP polynucleotide sequences.

Additionally contemplated are polynucleotides encoding NHP ORFs, or their functional equivalents, encoded by polynucleotide sequences that are about 99, 95, 90, or about 85 percent similar or identical to corresponding regions of the nucleotide sequences of the Sequence Listing (as measured by BLAST sequence comparison analysis using, for example, the GCG sequence analysis package (Madison, Wis.) using standard default settings).

The invention also includes nucleic acid molecules, preferably DNA molecules, that hybridize to, and are therefore the complements of, the described NHP nucleotide sequences. Such hybridization conditions may be highly stringent or less highly stringent, as described above. In instances where the nucleic acid molecules are deoxyoligonucleotides ("DNA oligos"), such molecules are generally about 16 to about 100 bases long, or about 20 to about 80, or about 34 to about 45 bases long, or any variation or combination of sizes represented therein that incorporate a contiguous region of sequence first disclosed in the Sequence Listing. Such oligonucleotides can be used in conjunction with the polymerase chain reaction (PCR) to screen libraries, isolate clones, and prepare cloning and sequencing templates, etc.

Alternatively, such NHP oligonucleotides can be used as hybridization probes for screening libraries, and assessing gene expression patterns (particularly using a micro array or high-throughput "chip" format). Additionally, a series of the described NHP oligonucleotide sequences, or the complements thereof, can be used to represent all or a portion of the described NHP sequences. An oligonucleotide or polynucleotide sequence first disclosed in at least a portion of one or more of the sequences of SEQ ID NOS: 1–17 can be used as a hybridization probe in conjunction with a solid support matrix/substrate (resins, beads, membranes, plastics, polymers, metal or metallized substrates, crystalline or polycrystalline substrates, etc.). Of particular note are spatially addressable arrays (i.e., gene chips, microtiter plates, etc.) of oligonucleotides and polynucleotides, or corresponding oligopeptides and polypeptides, wherein at least one of the biopolymers present on the spatially addressable array comprises an oligonucleotide or polynucleotide sequence first disclosed in at least one of the sequences of SEQ ID NOS: 1–17, or an amino acid sequence encoded thereby. Methods for attaching biopolymers to, or synthesizing biopolymers on, solid support matrices, and conducting binding studies thereon are disclosed in, inter alia, U.S. Pat. Nos. 5,700,637, 5,556,752, 5,744,305, 4,631,211, 5,445,934, 5,252,743, 4,713,326, 5,424,186, and 4,689,405 the disclosures of which are herein incorporated by reference in their entirety.

Addressable arrays comprising sequences first disclosed in SEQ ID NOS:1–17 can be used to identify and characterize the temporal and tissue specific expression of a gene. These addressable arrays incorporate oligonucleotide sequences of sufficient length to confer the required specificity, yet be within the limitations of the production technology. The length of these probes is within a range of between about 8 to about 2000 nucleotides. Preferably the probes consist of 60 nucleotides and more preferably 25 nucleotides from the sequences first disclosed in SEQ ID NOS:1–17.

For example, a series of the described oligonucleotide sequences, or the complements thereof, can be used in chip format to represent all or a portion of the described sequences. The oligonucleotides, typically between about 16 to about 40 (or any whole number within the stated range) nucleotides in length can partially overlap each other and/or the sequence may be represented using oligonucleotides that do not overlap. Accordingly, the described polynucleotide sequences shall typically comprise at least about two or three distinct oligonucleotide sequences of at least about 8 nucleotides in length that are each first disclosed in the described Sequence Listing. Such oligonucleotide sequences can begin at any nucleotide present within a sequence in the Sequence Listing and proceed in either a sense (5'-to-3') orientation vis-a-vis the described sequence or in an antisense orientation.

Microarray-based analysis allows the discovery of broad patterns of genetic activity, providing new understanding of gene functions and generating novel and unexpected insight into transcriptional processes and biological mechanisms. The use of addressable arrays comprising sequences first disclosed in SEQ ID NOS:1–17 provides detailed information about transcriptional changes involved in a specific pathway, potentially leading to the identification of novel components or gene functions that manifest themselves as novel phenotypes.

Probes consisting of sequences first disclosed in SEQ ID NOS:1–17 can also be used in the identification, selection and validation of novel molecular targets for drug discovery. The use of these unique sequences permits the direct confirmation of drug targets and recognition of drug dependent changes in gene expression that are modulated through pathways distinct from the drugs intended target. These unique sequences therefore also have utility in defining and monitoring both drug action and toxicity.

As an example of utility, the sequences first disclosed in SEQ ID NOS:1–17 can be utilized in microarrays or other assay formats, to screen collections of genetic material from patients who have a particular medical condition. These investigations can also be carried out using the sequences first disclosed in SEQ ID NOS:1–17 in silico and by comparing previously collected genetic databases and the disclosed sequences using computer software known to those in the art.

Thus the sequences first disclosed in SEQ ID NOS:1–17 can be used to identify mutations associated with a particular disease and also as a diagnostic or prognostic assay.

Although the presently described sequences have been specifically described using nucleotide sequence, it should be appreciated that each of the sequences can uniquely be described using any of a wide variety of additional structural attributes, or combinations thereof. For example, a given sequence can be described by the net composition of the nucleotides present within a given region of the sequence in conjunction with the presence of one or more specific oligonucleotide sequence(s) first disclosed in the SEQ ID NOS: 1–17. Alternatively, a restriction map specifying the relative positions of restriction endonuclease digestion sites, or various palindromic or other specific oligonucleotide sequences can be used to structurally describe a given sequence. Such restriction maps, which are typically generated by widely available computer programs (e.g., the University of Wisconsin GCG sequence analysis package, SEQUENCHER 3.0, Gene Codes Corp., Ann Arbor, Mich., etc.), can optionally be used in conjunction with one or more discrete nucleotide sequence(s) present in the sequence that can be described by the relative position of the sequence relatve to one or more additional sequence(s) or one or more restriction sites present in the disclosed sequence.

For oligonucleotide probes, highly stringent conditions may refer, e.g., to washing in 6× SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as NHP gene antisense molecules, useful, for example, in NHP gene regulation (for and/or as antisense primers in amplification reactions of NHP nucleic acid sequences). With respect to NHP gene regulation, such techniques can be used to regulate biological functions. Further, such sequences may be used as part of ribozyme and/or triple helix sequences that are also useful for NHP gene regulation.

Inhibitory antisense or double stranded oligonucleotides can additionally comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide can also comprise at least one modified sugar moiety selected from the group including but not limited to arabinose, 2-fluoroarabinose, xylulose, and hexose.

In yet another embodiment, the antisense oligonucleotide will comprise at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330). Alternatively, double stranded RNA can be used to disrupt the expression and function of a targeted NHP.

Oligonucleotides of the invention can be synthesized by standard methods known in the art, e.g. by use of an automated DNA synthesizer (such as are commercially available from Biosearch, Applied Biosystems, etc.). As examples, phosphorothioate oligonucleotides can be synthesized by the method of Stein et al. (1988, Nucl. Acids Res. 16:3209), and methylphosphonate oligonucleotides can be prepared by use of controlled pore glass polymer supports (Sarin et al., 1988, Proc. Natl. Acad. Sci. U.S.A. 85:7448–7451), etc.

Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual (and periodic updates thereof), Cold Springs Harbor Press, N.Y.; and Ausubel et al., 1989, Current Protocols in Molecular Biology, Green Publishing Associates and Wiley Interscience, N.Y.

Alternatively, suitably labeled NHP nucleotide probes can be used to screen a human genomic library using appropriately stringent conditions or by PCR. The identification and characterization of human genomic clones is helpful for identifying polymorphisms (including, but not limited to, nucleotide repeats, microsatellite alleles, single nucleotide polymorphisms, or coding single nucleotide polymorphisms), determining the genomic structure of a given locus/allele, and designing diagnostic tests. For example, sequences derived from regions adjacent to the intron/exon boundaries of the human gene can be used to design primers for use in amplification assays to detect mutations within the exons, introns, splice sites (e.g., splice acceptor and/or donor sites), etc., that can be used in diagnostics and pharmacogenomics.

Further, a NHP gene homolog can be isolated from nucleic acid from an organism of interest by performing PCR using two degenerate or "wobble" oligonucleotide primer pools designed on the basis of amino acid sequences within the NHP products disclosed herein. The template for the reaction may be total RNA, mRNA, and/or cDNA obtained by reverse transcription of mRNA prepared from human or non-human cell lines or tissue known or suspected to express an allele of a NHP gene.

The PCR product can be subcloned and sequenced to ensure that the amplified sequences represent the sequence of the desired NHP gene. The PCR fragment can then be used to isolate a full length cDNA clone by a variety of methods. For example, the amplified fragment can be labeled and used to screen a cDNA library, such as a bacteriophage cDNA library. Alternatively, the labeled fragment can be used to isolate genomic clones via the screening of a genomic library.

PCR technology can also be used to isolate full length cDNA sequences. For example, RNA can be isolated, following standard procedures, from an appropriate cellular or tissue source (i.e., one known, or suspected, to express a NHP gene). A reverse transcription (RT) reaction can be performed on the RNA using an oligonucleotide primer specific for the most 5' end of the amplified fragment for the priming of first strand synthesis. The resulting RNA/DNA hybrid may then be "tailed" using a standard terminal transferase reaction, the hybrid may be digested with RNase H, and second strand synthesis may then be primed with a complementary primer. Thus, cDNA sequences upstream of the amplified fragment can be isolated. For a review of cloning strategies that can be used, see e.g., Sambrook et al., 1989, supra.

A cDNA encoding a mutant NHP gene can be isolated, for example, by using PCR. In this case, the first cDNA strand may be synthesized by hybridizing an oligo-dT oligonucleotide to mRNA isolated from tissue known or suspected to be expressed in an individual putatively carrying a mutant NHP allele, and by extending the new strand with reverse transcriptase. The second strand of the cDNA is then synthesized using an oligonucleotide that hybridizes specifically to the 5' end of the normal gene. Using these two primers, the product is then amplified via PCR, optionally cloned into a suitable vector, and subjected to DNA sequence analysis through methods well known to those of skill in the art. By comparing the DNA sequence of the mutant NHP allele to that of a corresponding normal NHP allele, the mutation(s) responsible for the loss or alteration of function of the mutant NHP gene product can be ascertained.

Alternatively, a genomic library can be constructed using DNA obtained from an individual suspected of or known to carry a mutant NHP allele (e.g., a person manifesting a NHP-associated phenotype such as, for example, obesity, vision disorders, high blood pressure, depression, infertility, etc.), or a cDNA library can be constructed using RNA from a tissue known, or suspected, to express a mutant NHP allele. A normal NHP gene, or any suitable fragment thereof, can then be labeled and used as a probe to identify the corresponding mutant NHP allele in such libraries. Clones containing mutant NHP gene sequences can then be purified and subjected to sequence analysis according to methods well known to those skilled in the art.

Additionally, an expression library can be constructed utilizing cDNA synthesized from, for example, RNA isolated from a tissue known, or suspected, to express a mutant NHP allele in an individual suspected of or known to carry such a mutant allele. In this manner, gene products made by the putatively mutant tissue can be expressed and screened using standard antibody screening techniques in conjunction with antibodies raised against a normal NHP product, as described below. (For screening techniques, see, for example, Harlow, E. and Lane, eds., 1988, "Antibodies: A Laboratory Manual", Cold Spring Harbor Press, Cold Spring Harbor.) Additionally, screening can be accomplished by screening with labeled NHP fusion proteins, such as, for example, alkaline phosphatase-NHP or NHP-alkaline phosphatase fusion proteins. In cases where a NHP mutation results in an expressed gene product with altered function (e.g., as a result of a missense or a frameshift mutation), polyclonal antibodies to a NHP are likely to cross-react with a corresponding mutant NHP gene product. Library clones detected via their reaction with such labeled antibodies can be purified and subjected to sequence analysis according to methods well known in the art.

The invention also encompasses (a) DNA vectors that contain any of the foregoing NHP coding sequences and/or their complements (i.e., antisense); (b) DNA expression vectors that contain any of the foregoing NHP coding sequences operatively associated with a regulatory element that directs the expression of the coding sequences (for example, baculo virus as described in U.S. Pat. No. 5,869,336 herein incorporated by reference); (c) genetically engineered host cells that contain any of the foregoing NHP coding sequences operatively associated with a regulatory element that directs the expression of the coding sequences in the host cell; and (d) genetically engineered host cells that express an endogenous NHP gene under the control of an exogenously introduced regulatory element (i.e., gene activation). As used herein, regulatory elements include, but are not limited to, inducible and non-inducible promoters, enhancers, operators and other elements known to those skilled in the art that drive and regulate expression. Such regulatory elements include but are not limited to the cytomegalovirus (hCMV) immediate early gene, regulatable, viral elements (particularly retroviral LTR promoters), the early or late promoters of SV40 adenovirus, the lac system, the trp system, the TAC system, the TRC system, the major operator and promoter regions of phage lambda, the control regions of fd coat protein, the promoter for 3-phosphoglycerate kinase (PGK), the promoters of acid phosphatase, and the promoters of the yeast a-mating factors.

The present invention also encompasses antibodies and anti-idiotypic antibodies (including Fab fragments), antagonists and agonists of the NHP, as well as compounds or nucleotide constructs that inhibit expression of a NHP gene (transcription factor inhibitors, antisense and ribozyme molecules, or gene or regulatory sequence replacement constructs), or promote the expression of a NHP (e.g., expression constructs in which NHP coding sequences are operatively associated with expression control elements such as promoters, promoter/enhancers, etc.).

The NHPs or NHP peptides, NHP fusion proteins, NHP nucleotide sequences, antibodies, antagonists and agonists can be useful for the detection of mutant NHPs or inappropriately expressed NHPs for the diagnosis of disease. The NHP proteins or peptides, NHP fusion proteins, NHP nucleotide sequences, host cell expression systems, antibodies, antagonists, agonists and genetically engineered cells and animals can be used for screening for drugs (or high throughput screening of combinatorial libraries) effective in the treatment of the symptomatic or phenotypic manifestations of perturbing the normal function of NHP in the body. The use of engineered host cells and/or animals may offer an advantage in that such systems allow not only for the identification of compounds that bind to the endogenous receptor for an NHP, but can also identify compounds that trigger NHP-mediated activities or pathways.

Finally, the NHP products can be used as therapeutics. For example, soluble derivatives such as NHP peptides/domains corresponding to the NHPs, NHP fusion protein products (especially NHP-Ig fusion proteins, i.e., fusions of a NHP, or a domain of a NHP, to an IgFc), NHP antibodies and anti-idiotypic antibodies (including Fab fragments), antagonists or agonists (including compounds that modulate or act on downstream targets in a NHP-mediated pathway) can be used to directly treat diseases or disorders. For instance, the administration of an effective amount of soluble NHP, or a NHP-IgFc fusion protein or an anti-idiotypic antibody (or its Fab) that mimics the NHP could activate or effectively antagonize the endogenous NHP receptor. Nucleotide constructs encoding such NHP products can be used to genetically engineer host cells to express such products in vivo; these genetically engineered cells function as "bioreactors" in the body delivering a continuous supply of a NHP, a NHP peptide, or a NHP fusion protein to the body. Nucleotide constructs encoding functional NHPs, mutant NHPs, as well as antisense and ribozyme molecules can also be used in "gene therapy" approaches for the modulation of NHP expression. Thus, the invention also encompasses pharmaceutical formulations and methods for treating biological disorders.

Various aspects of the invention are described in greater detail in the subsections below.

5.1 The NHP Sequences

The cDNA sequences and the corresponding deduced amino acid sequences of the described NHPs are presented in the Sequence Listing. The NHP nucleotides were obtained from clustered human gene trapped sequences, ESTs, and cDNA isolated from human lymph node, pituitary, placenta, trachea and mammary gland cDNA cell libraries (Edge Biosystems, Gaithersburg, Md.). The described sequences share limited structural similarity with a variety of proteins, including, but not limited to, proteinases, thrombospondin-1, F-spondin, ADAMTS metalloproteases, Tango-71, and distintegrins.

5.2 NHPs and NHP Polypeptides

NHPs, polypeptides, peptide fragments, mutated, truncated, or deleted forms of the NHPs, and/or NHP fusion proteins can be prepared for a variety of uses. These uses include but are not limited to the generation of antibodies, as reagents in diagnostic assays, the identification of other cellular gene products related to a NHP, as reagents in assays for screening for compounds that can be as pharmaceutical reagents useful in the therapeutic treatment of mental, biological, or medical disorders and diseases. Given the similarity information and expression data, the described NHPs can be targeted (by drugs, oligos, antibodies, etc,) in order to treat disease, or to therapeutically augment the efficacy of therapeutic agents.

The Sequence Listing discloses the amino acid sequences encoded by the described NHP polynucleotide sequences. The NHPs typically display initiator methionines in DNA sequence contexts consistent with a translation initiation site, and a signal sequence characteristic of membrane or secreted proteins.

The NHP amino acid sequences of the invention include the amino acid sequences presented in the Sequence Listing as well as analogues and derivatives thereof. Further, corresponding NHP homologues from other species are encompassed by the invention. In fact, any NHP protein encoded by the NHP nucleotide sequences described above are within the scope of the invention, as are any novel polynucleotide sequences encoding all or any novel portion of an amino acid sequence presented in the Sequence Listing. The degenerate nature of the genetic code is well known, and, accordingly, each amino acid presented in the Sequence Listing, is generically representative of the well known nucleic acid "triplet" codon, or in many cases codons, that can encode the amino acid. As such, as contemplated herein, the amino acid sequences presented in the Sequence Listing, when taken together with the genetic code (see, for example, Table 4-1 at page 109 of "Molecular Cell Biology", 1986, J. Darnell et al. eds., Scientific American Books, New York, N.Y., herein incorporated by reference) are generically representative of all the various permutations and combinations of nucleic acid sequences that can encode such amino acid sequences.

The invention also encompasses proteins that are functionally equivalent to the NHPs encoded by the presently described nucleotide sequences as judged by any of a number of criteria, including, but not limited to, the ability to bind and cleave a substrate of a NHP, or the ability to effect an identical or complementary downstream pathway, or a change in cellular metabolism (e.g., proteolytic activity, ion flux, tyrosine phosphorylation, transport, etc.). Such functionally equivalent NHP proteins include, but are not limited to, additions or substitutions of amino acid residues within the amino acid sequence encoded by the NHP nucleotide sequences described above, but which result in a silent change, thus producing a functionally equivalent gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

A variety of host-expression vector systems can be used to express the NHP nucleotide sequences of the invention. Where, as in the present instance, the NHP peptide or polypeptide is thought to be membrane protein, the hydrophobic regions of the protein can be excised and the resulting soluble peptide or polypeptide can be recovered from the culture media. Such expression systems also encompass engineered host cells that express a NHP, or functional equivalent, in situ. Purification or enrichment of a NHP from such expression systems can be accomplished using appropriate detergents and lipid micelles and methods well known to those skilled in the art. However, such engineered host cells themselves may be used in situations where it is important not only to retain the structural and functional characteristics of the NHP, but to assess biological activity, e.g., in drug screening assays.

The expression systems that can be used for purposes of the invention include but are not limited to microorganisms such as bacteria (e.g., *E. coli, B. subtilis*) transformed with recombinant bacteriophage DNA, plasmid DNA or cosmid DNA expression vectors containing NHP nucleotide sequences; yeast (e.g., Saccharomyces, Pichia) transformed with recombinant yeast expression vectors containing NHP nucleotide sequences; insect cell systems infected with recombinant virus expression vectors (e.g., baculovirus) containing NHP sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing NHP nucleotide sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the NHP product being expressed. For example, when a large quantity of such a protein is to be produced for the generation of pharmaceutical compositions of or containing NHP, or for raising antibodies to a NHP, vectors that direct the expression of high levels of fusion protein products that are readily purified may be desirable. Such vectors include, but are not limited, to the *E. coli* expression vector pUR278 (Ruther et al., 1983, EMBO J. 2:1791), in which a NHP coding sequence may be ligated individually into the vector in frame with the lacZ coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors (Pharmacia or American Type Culture Collection) can also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety.

In an insect system, *Autographa califormica* nuclear polyhidrosis virus (AcNPV) is used as a vector to express foreign genes. The virus grows in *Spodoptera frugiperda* cells. A NHP coding sequence may be cloned individually into non-essential regions (for example the polyhedrin gene) of the virus and placed under control of an AcNPV promoter (for example the polyhedrin promoter). Successful insertion of NHP coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed (e.g., see Smith et al., 1983, J. Virol. 46:584; Smith, U.S. Pat. No. 4,215,051).

In mammalian host cells, a number of viral-based expression systems may be utilized. In cases where an adenovirus is used as an expression vector, the NHP nucleotide sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing a NHP product in infected hosts (e.g., See Logan & Shenk, 1984, Proc. Natl. Acad. Sci. USA 81:3655–3659). Specific initiation signals may also be required for efficient translation of inserted NHP nucleotide sequences. These signals include the ATG initiation codon and adjacent sequences. In cases where an entire NHP gene or cDNA, including its own initiation codon and adjacent sequences, is inserted into the appropriate expression vector, no additional translational control signals may be needed. However, in cases where only a portion of a NHP coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See Bittner et al., 1987, Methods in Enzymol. 153:516–544).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, VERO, BHK, HeLa, COS, MDCK, 293, 3T3, WI38, and in particular, human cell lines.

For long-term, high-yield production of recombinant proteins, stable expression is preferred. For example, cell lines which stably express the NHP sequences described above can be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the NHP product. Such engineered cell lines may be particularly useful in screening and evaluation of compounds that affect the endogenous activity of the NHP product.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk, hgprt or aprt cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

Alternatively, any fusion protein can be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88:8972–8976). In this system, the polynucleotide sequence of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$.nitriloacetic acid-agarose columns and histidine-tagged proteins are selectively eluted with imidazole-containing buffers.

Also encompassed by the present invention are fusion proteins that direct the NHP to a target organ and/or facilitate transport across the membrane into the cytosol. Conjugation of NHPs to antibody molecules or their Fab fragments could be used to target cells bearing a particular epitope. Attaching the appropriate signal sequence to the NHP would also transport the NHP to the desired location within the cell. Alternatively targeting of NHP or its nucleic acid sequence might be achieved using liposome or lipid complex based delivery systems. Such technologies are described in *Liposomes: A Practical Approach*, New, RRC ed., Oxford University Press, New York and in U.S. Pat. Nos. 4,594,595, 5,459,127, 5,948,767 and 6,110,490 and their respective disclosures which are herein incorporated by reference in their entirety. Additionally embodied are novel protein constructs engineered in such a way that they facilitate transport of the NHP to the target site or desired organ, where they cross the cell membrane and/or the nucleus where the NHP can exert its functional activity. This goal may be achieved by coupling of the NHP to a cytokine or other ligand that provides targeting specificity, and/or to a protein transducing domain (see generally U.S. applications Ser. No. 60/111,701 and 60/056,713, both of which are herein incorporated by reference, for examples of such transducing sequences) to facilitate passage across cellular membranes and can optionally be engineered to include nuclear localization sequences.

5.3 Antibodies To NHP Products

Antibodies that specifically recognize one or more epitopes of a NHP, or epitopes of conserved variants of a NHP, or peptide fragments of a NHP are also encompassed by the invention. Such antibodies include but are not limited to polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above.

The antibodies of the invention may be used, for example, in the detection of NHP in a biological sample and may, therefore, be utilized as part of a diagnostic or prognostic technique whereby patients may be tested for abnormal amounts of NHP. Such antibodies may also be utilized in conjunction with, for example, compound screening schemes for the evaluation of the effect of test compounds on expression and/or activity of a NHP gene product. Additionally, such antibodies can be used in conjunction gene therapy to, for example, evaluate the normal and/or engineered NHP-expressing cells prior to their introduction into the patient. Such antibodies may additionally be used as a method for the inhibition of abnormal NHP activity. Thus, such antibodies may, therefore, be utilized as part of treatment methods.

For the production of antibodies, various host animals may be immunized by injection with the NHP, an NHP peptide (e.g., one corresponding to a functional domain of an NHP), truncated NHP polypeptides (NHP in which one or more domains have been deleted), functional equivalents of the NHP or mutated variant of the NHP. Such host animals may include but are not limited to pigs, rabbits, mice, goats, and rats, to name but a few. Various adjuvants may be used to increase the immunological response, depending on the host species, including but not limited to Freund's adjuvant (complete and incomplete), mineral salts such as aluminum hydroxide or aluminum phosphate, surface active substances such as lysolecithin, pluronic polyols, polyanions, peptides, oil emulsions, and potentially useful human adjuvants such as BCG (bacille Calmette-Guerin) and *Corynebacterium parvum*. Alternatively, the immune response could be enhanced by combination and or coupling with molecules such as keyhole limpet hemocyanin, tetanus toxoid, diptheria toxoid, ovalbumin, cholera toxin or fragments thereof. Polyclonal antibodies are heterogeneous populations of antibody molecules derived from the sera of the immunized animals.

Monoclonal antibodies, which are homogeneous populations of antibodies to a particular antigen, can be obtained by any technique which provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. Such technologies are described in U.S. Pat. Nos. 6,075,181 and 5,877,397 and their respective disclosures which are herein incorporated by reference in their entirety. Also encompassed by the present invention is the use of fully humanized monoclonal antibodies as described in U.S. Pat. No. 6,150,584 and respective disclosures which are herein incorporated by reference in their entirety.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce single chain antibodies against NHP gene products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include, but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity.

Antibodies to a NHP can, in turn, be utilized to generate anti-idiotype antibodies that "mimic" a given NHP, using techniques well known to those skilled in the art. (See, e.g., Greenspan & Bona, 1993, FASEB J 7(5):437–444; and Nissinoff, 1991, J. Immunol. 147(8):2429–2438). For example antibodies which bind to a NHP domain and competitively inhibit the binding of NHP to its cognate receptor can be used to generate anti-idiotypes that "mimic" the NHP and, therefore, bind and activate or neutralize a receptor. Such anti-idiotypic antibodies or Fab fragments of such anti-idiotypes can be used in therapeutic regimens involving a NHP mediated pathway.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims. All cited publications, patents, and patent applications are herein incorporated by reference in their entirety.

We claim:

1. An isolated nucleic acid molecule comprising the nucleotide sequence of SEQ ID NO:1.

2. An isolated nucleic acid molecule comprising a nucleotide sequence that encodes the amino acid sequence shown in SEQ ID NO: 2.

3. A recombinant expression vector comprising the isolated nucleic acid molecule of claim 2.

4. The recombinant expression vector of claim 3, wherein the isolated nucleic acid molecule comprises the nucleotide sequence of SEQ ID NO:1.

5. A host cell comprising the recombinant expression vector of claim 3.

* * * * *

SEQUENCE LISTING

<160> NUMBER OF SEQ ID NOS: 17

<210> SEQ ID NO 1
<211> LENGTH: 5076
<212> TYPE: DNA
<213> ORGANISM: homo sapiens

<400> SEQUENCE: 1

| | | | | | |
|---|---|---|---|---|---|
| atggcttcct | ggacgagccc | ctggtgggtg | ctgatagggA | tggtcttcat | gcactctccc | 60 |
| ctcccgcaga | ccacagctga | gaaatctcct | ggagcctatt | tccttcccga | gtttgcactt | 120 |
| tctcctcagg | gaagttttct | ggaagacaca | acagggagc | agttcctcac | ttatcgctat | 180 |
| gatgaccaga | cctcaagaaa | cactcgttca | gatgaagaca | agatggcaa | ctgggatgct | 240 |
| tggggcgact | ggagtgactg | ctcccggacc | tgtgggggag | gagcatcata | ttctctgcgg | 300 |
| agatgtttga | ctggaaggaa | ttgtgaaggg | cagaacattc | ggtacaagac | atgcagcaat | 360 |
| catgactgcc | ctccagatgc | agaagatttc | agagcccagc | agtgctcagc | ctacaatgat | 420 |
| gtccagtatc | agggcatta | ctatgaatgg | cttccacgat | ataatgatcc | tgctgccccg | 480 |
| tgtgcactca | agtgtcatgc | acaaggacaa | aacttggtgg | tggagctggc | acctaaggta | 540 |
| ctggatggaa | ctcgttgcaa | cacggactcc | ttggacatgt | gtatcagtgg | catctgtcag | 600 |
| gcagtgggct | gcgatcggca | actgggaagc | aatgccaagg | aggacaactg | tggagtctgt | 660 |
| gccggcgatg | gctccacctg | caggcttgta | cgggacaat | caaagtcaca | cgtttctcct | 720 |
| gaaaaaagag | aagaaaatgt | aattgctgtt | cctttgggaa | gtcgaagtgt | gagaattaca | 780 |
| gtgaaaggac | ctgcccacct | ctttattgaa | tcaaaaacac | ttcaaggaag | caaggagaa | 840 |
| cacagcttta | acagccccgg | cgtctttgtc | gtagaaaaca | caacagtgga | atttcagagg | 900 |
| ggctccgaga | ggcaaacttt | taagattcca | ggacctctga | tggctgattt | catcttcaag | 960 |
| accaggtaca | ctgcagccaa | agacagcgtg | gttcagttct | tcttttacca | gcccatcagt | 1020 |
| catcagtgga | gacaaactga | cttctttccc | tgcactgtga | cgtgtggagg | aggttatcag | 1080 |
| ctcaattctg | ctgaatgtgt | ggatatccgc | ttgaagaggg | tagttcctga | ccattattgt | 1140 |
| cactactacc | ctgaaaatgt | aaaaccaaaa | ccaaaactga | aggaatgcag | catggatccc | 1200 |
| tgcccatcaa | gtgatggatt | taaagagata | atgcccatg | accacttcca | acctcttcct | 1260 |
| cgctgggaac | ataatccttg | gactgcatgt | tccgtgtcct | gtgaggagg | gattcagaga | 1320 |
| cggagctttg | tgtgtgtaga | ggaatccatg | catggagaga | tattgcaggt | ggaagaatgg | 1380 |
| aagtgcatgt | acgcacccaa | acccaaggtt | atgcaaactt | gtaatctgtt | tgattgcccc | 1440 |
| aagtggattg | ccatggagtg | gtctcagtgc | acagtgactt | gtggccgagg | gttacggtac | 1500 |
| cgggttgttc | tgtgtattaa | ccaccgcgga | gagcatgttg | ggggctgcaa | tccacaactg | 1560 |
| aagttacaca | tcaaagaaga | atgtgtcatt | cccatcccgt | gttataaacc | aaaagaaaaa | 1620 |
| agtccagtgg | aagcaaaatt | gccttggctg | aaacaagcac | aagaactaga | agagaccaga | 1680 |
| atagcaacag | aagaaccaac | gttcattcca | gaaccctggt | cagcctgcag | taccacgtgt | 1740 |
| gggccaggtg | tgcaggtccg | cgaggtgaag | tgccgtgtgc | tcctcacatt | cacgcagact | 1800 |
| gagactgagc | tgcccgagga | agagtgtgaa | ggccccaagc | tgcccaccga | acggcctgc | 1860 |
| ctcctggaag | catgtgatga | gagcccggcc | tcccgagagc | tagacatccc | tctccctgag | 1920 |
| gacagtgaga | cgacttacga | ctgggagtac | gctgggttca | ccccttgcac | agcaacatgc | 1980 |
| ttgggaggcc | atcaagaagc | catagcagtg | tgcttacata | tccagaccca | gcagacagtc | 2040 |

-continued

```
aatgacagct tgtgtgatat ggtccaccgt cctccagcca tgagccaggc ctgtaacaca    2100
gagccctgtc cccccaggtg gcatgtgggc tcttgggggc cctgctcagc tacctgtgga    2160
gttggaattc agacccgaga tgtgtactgc ctgcacccag gggagacccc tgcccctcct    2220
gaggagtgcc gagatgaaaa gccccatgct ttacaagcat gcaatcagtt tgactgccct    2280
cctggctggc acattgaaga atggcagcag tgttccagga cttgtggcgg gggaactcag    2340
aacagaagag tcacctgtcg gcagctgcta acggatggca gctttttgaa tctctcagat    2400
gaattgtgcc aaggacccaa ggcatcgtct cacaagtcct gtgccaggac agactgtcct    2460
ccacatttag ctgtgggaga ctggtcgaag tgttctgtca gttgtggtgt tggaatccag    2520
agaagaaagc aggtgtgtca aaggctggca gccaaaggtc ggcgcatccc cctcagtgag    2580
atgatgtgca gggatctacc agggttccct cttgtaagat cttgccagat gcctgagtgc    2640
agtaaaatca aatcagagat gaagacaaaa cttggtgagc agggtccgca gatcctcagt    2700
gtccagagag tctacattca gacaagggaa gagaagcgta ttaacctgac cattggtagc    2760
agagcctatt gctgcccaa cacatccgtg attattaagt gccccgtgcg acgattccag    2820
aaatctctga tccagtggga aaggatggc cgttgcctgc agaactccaa acggcttggc    2880
atcaccaagt caggctcact aaaaatccac ggtcttgctg cccccgacat cggcgtgtac    2940
cggtgcattg caggctctgc acaggaaaca gttgtgctca agctcattgg tactgacaac    3000
cggctcatcg cacgcccagc cctcaggag cctatgaggg aatatcctgg gatggaccac    3060
agcgaagcca atagtttggg agtcacatgg cacaaaatga ggcaaatgtg gaataacaaa    3120
aatgaccttt atctggatga tgaccacatt agtaaccagc cttttcttgag agctctgtta    3180 ggccactgca gcaattctgc aggaagcacc aactcctggg agttgaagaa taagcagttt    3240
gaagcagcag ttaaacaagg agcatatagc atggatacag cccagtttga tgagctgata    3300
agaaacatga gtcagctcat ggaaaccgga gaggtcagcg atgatcttgc gtcccagctg    3360
atatatcagc tggtggccga attagccaag gcacagccaa cacacatgca gtggcggggc    3420
atccaggaag agacacctcc tgctgctcag ctcagagggg aaacagggag tgtgtcccaa    3480
agctcgcatg caaaaaactc aggcaagctg acattcaagc cgaaaggacc tgttctcatg    3540
aggcaaagcc aacctccctc aatttcattt aataaaacaa taaattccag gattggaaat    3600
acagtataca ttcaaaaaag gacagaggtc atcaatatac tgtgtgacct tattccccc    3660 agtgaggcca catatacatg gaccaaggat ggaaccttgt tacagccctc agtaaaaata    3720
attttggatg gaactgggaa gatacagata cagaatccta caaggaaaga acaaggcata    3780
tatgaatgtt ctgtagctaa tcatcttggt tcagatgtgg aaagttcttc tgtgctgtat    3840
gcagaggcac ctgtcatctt gtctgttgaa agaaatatca ccaaaccaga gcacaaccat    3900
ctgtctgttg tggttggagg catcgtggag gcagcccttg gagcaaacgt gacaatccga    3960
tgtcctgtaa aggtgtccc tcagcctaat ataacttggt tgaagagagg aggatctctg    4020
agtggcaatg tttccttgct tttcaatgga tccctgttgt tgcagaatgt ttcccttgaa    4080
aatgaaggaa cctacgtctg catagccacc aatgctcttg gaaaggcagt ggcaacatct    4140
gtactccact tgctggaacg aagatggcca gagagtagaa tcgtatttct gcaaggacat    4200
aaaaagtaca ttctccaggc aaccaacact agaaccaaca gcaatgaccc aacaggagaa    4260
cccccgcctc aagagccttt tgggagcct ggtaactggt cacattgttc tgccacctgt    4320
ggtcatttgg gagcccgcat tcagagaccc cagtgtgtga tggccaatgg gcaggaagtg    4380
```

-continued

```
agtgaggccc tgtgtgatca cctccagaag ccactggctg ggtttgagcc ctgtaacatc      4440
cgggactgcc cagcgaggtg gttcacaagt gtgtggtcac agtgctctgt gtcttgcggt      4500
gaaggatacc acagtcggca ggtgacgtgc aagcggacaa aagccaatgg aactgtgcag      4560
gtggtgtctc caagagcatg tgcccctaaa gaccggcctc tgggaagaaa accatgtttt      4620
ggtcatccat gtgttcagtg gaaccaggg aaccggtgtc ctggacgttg catgggccgt      4680
gctgtgagga tgcagcagcg tcacacagct tgtcaacaca acagctctga ctccaactgt      4740
gatgacagaa agagacccac cttaagaagg aactgcacat caggggcctg tgatgtgtgt      4800
tggcacacag gcccttggaa gccctgtaca gcagcctgtg gcaggggttt ccagtctcgg      4860
aaagtcgact gtatccacac aaggagttgc aaacctgtgg ccaagagaca ctgtgtacag      4920
aaaaagaaac caatttcctg gcggcactgt cttgggccct cctgtgatag agactgcaca      4980
gacacaactc actactgtat gtttgtaaaa catcttaatt tgtgttctct agaccgctac      5040
aaacaaaggt gctgccagtc atgtcaagag ggataa                                5076
```

<210> SEQ ID NO 2
<211> LENGTH: 1691
<212> TYPE: PRT
<213> ORGANISM: homo sapiens

<400> SEQUENCE: 2

```
Met Ala Ser Trp Thr Ser Pro Trp Trp Val Leu Ile Gly Met Val Phe
 1               5                   10                  15

Met His Ser Pro Leu Pro Gln Thr Thr Ala Glu Lys Ser Pro Gly Ala
                20                  25                  30

Tyr Phe Leu Pro Glu Phe Ala Leu Ser Pro Gln Gly Ser Phe Leu Glu
            35                  40                  45

Asp Thr Thr Gly Glu Gln Phe Leu Thr Tyr Arg Tyr Asp Asp Gln Thr
        50                  55                  60

Ser Arg Asn Thr Arg Ser Asp Glu Asp Lys Asp Gly Asn Trp Asp Ala
65                  70                  75                  80

Trp Gly Asp Trp Ser Asp Cys Ser Arg Thr Cys Gly Gly Gly Ala Ser
                85                  90                  95

Tyr Ser Leu Arg Arg Cys Leu Thr Gly Arg Asn Cys Glu Gly Gln Asn
            100                 105                 110

Ile Arg Tyr Lys Thr Cys Ser Asn His Asp Cys Pro Pro Asp Ala Glu
        115                 120                 125

Asp Phe Arg Ala Gln Gln Cys Ser Ala Tyr Asn Asp Val Gln Tyr Gln
130                 135                 140

Gly His Tyr Tyr Glu Trp Leu Pro Arg Tyr Asn Asp Pro Ala Ala Pro
145                 150                 155                 160

Cys Ala Leu Lys Cys His Ala Gln Gly Gln Asn Leu Val Val Glu Leu
                165                 170                 175

Ala Pro Lys Val Leu Asp Gly Thr Arg Cys Asn Thr Asp Ser Leu Asp
            180                 185                 190

Met Cys Ile Ser Gly Ile Cys Gln Ala Val Gly Cys Asp Arg Gln Leu
        195                 200                 205

Gly Ser Asn Ala Lys Glu Asp Asn Cys Gly Val Cys Ala Gly Asp Gly
    210                 215                 220

Ser Thr Cys Arg Leu Val Arg Gly Gln Ser Lys Ser His Val Ser Pro
225                 230                 235                 240

Glu Lys Arg Glu Glu Asn Val Ile Ala Val Pro Leu Gly Ser Arg Ser
                245                 250                 255
```

-continued

Val Arg Ile Thr Val Lys Gly Pro Ala His Leu Phe Ile Glu Ser Lys
            260                 265                 270

Thr Leu Gln Gly Ser Lys Gly Glu His Ser Phe Asn Ser Pro Gly Val
        275                 280                 285

Phe Val Val Glu Asn Thr Thr Val Glu Phe Gln Arg Gly Ser Glu Arg
    290                 295                 300

Gln Thr Phe Lys Ile Pro Gly Pro Leu Met Ala Asp Phe Ile Phe Lys
305                 310                 315                 320

Thr Arg Tyr Thr Ala Ala Lys Asp Ser Val Val Gln Phe Phe Phe Tyr
                325                 330                 335

Gln Pro Ile Ser His Gln Trp Arg Gln Thr Asp Phe Phe Pro Cys Thr
            340                 345                 350

Val Thr Cys Gly Gly Gly Tyr Gln Leu Asn Ser Ala Glu Cys Val Asp
        355                 360                 365

Ile Arg Leu Lys Arg Val Val Pro Asp His Tyr Cys His Tyr Tyr Pro
    370                 375                 380

Glu Asn Val Lys Pro Lys Pro Lys Leu Lys Glu Cys Ser Met Asp Pro
385                 390                 395                 400

Cys Pro Ser Ser Asp Gly Phe Lys Glu Ile Met Pro Tyr Asp His Phe
                405                 410                 415

Gln Pro Leu Pro Arg Trp Glu His Asn Pro Trp Thr Ala Cys Ser Val
            420                 425                 430

Ser Cys Gly Gly Gly Ile Gln Arg Arg Ser Phe Val Cys Val Glu Glu
        435                 440                 445

Ser Met His Gly Glu Ile Leu Gln Val Glu Trp Lys Cys Met Tyr
450                 455                 460

Ala Pro Lys Pro Lys Val Met Gln Thr Cys Asn Leu Phe Asp Cys Pro
465                 470                 475                 480

Lys Trp Ile Ala Met Glu Trp Ser Gln Cys Thr Val Thr Cys Gly Arg
                485                 490                 495

Gly Leu Arg Tyr Arg Val Val Leu Cys Ile Asn His Arg Gly Glu His
            500                 505                 510

Val Gly Gly Cys Asn Pro Gln Leu Lys Leu His Ile Lys Glu Glu Cys
    515                 520                 525

Val Ile Pro Ile Pro Cys Tyr Lys Pro Lys Glu Lys Ser Pro Val Glu
530                 535                 540

Ala Lys Leu Pro Trp Leu Lys Gln Ala Gln Glu Leu Glu Glu Thr Arg
545                 550                 555                 560

Ile Ala Thr Glu Glu Pro Thr Phe Ile Pro Glu Pro Trp Ser Ala Cys
                565                 570                 575

Ser Thr Thr Cys Gly Pro Gly Val Gln Val Arg Glu Val Lys Cys Arg
            580                 585                 590

Val Leu Leu Thr Phe Thr Gln Thr Glu Thr Glu Leu Pro Glu Glu Glu
        595                 600                 605

Cys Glu Gly Pro Lys Leu Pro Thr Glu Arg Pro Cys Leu Leu Glu Ala
    610                 615                 620

Cys Asp Glu Ser Pro Ala Ser Arg Glu Leu Asp Ile Pro Leu Pro Glu
625                 630                 635                 640

Asp Ser Glu Thr Thr Tyr Asp Trp Glu Tyr Ala Gly Phe Thr Pro Cys
                645                 650                 655

Thr Ala Thr Cys Leu Gly Gly His Gln Glu Ala Ile Ala Val Cys Leu
            660                 665                 670

```
His Ile Gln Thr Gln Gln Thr Val Asn Asp Ser Leu Cys Asp Met Val
        675                 680                 685

His Arg Pro Pro Ala Met Ser Gln Ala Cys Asn Thr Glu Pro Cys Pro
    690                 695                 700

Pro Arg Trp His Val Gly Ser Trp Gly Pro Cys Ser Ala Thr Cys Gly
705                 710                 715                 720

Val Gly Ile Gln Thr Arg Asp Val Tyr Cys Leu His Pro Gly Glu Thr
                725                 730                 735

Pro Ala Pro Pro Glu Glu Cys Arg Asp Glu Lys Pro His Ala Leu Gln
            740                 745                 750

Ala Cys Asn Gln Phe Asp Cys Pro Pro Gly Trp His Ile Glu Glu Trp
        755                 760                 765

Gln Gln Cys Ser Arg Thr Cys Gly Gly Thr Gln Asn Arg Arg Val
    770                 775                 780

Thr Cys Arg Gln Leu Leu Thr Asp Gly Ser Phe Leu Asn Leu Ser Asp
785                 790                 795                 800

Glu Leu Cys Gln Gly Pro Lys Ala Ser His Lys Ser Cys Ala Arg
                805                 810                 815

Thr Asp Cys Pro Pro His Leu Ala Val Gly Asp Trp Ser Lys Cys Ser
                820                 825                 830

Val Ser Cys Gly Val Gly Ile Gln Arg Arg Lys Gln Val Cys Gln Arg
        835                 840                 845

Leu Ala Ala Lys Gly Arg Arg Ile Pro Leu Ser Glu Met Met Cys Arg
    850                 855                 860

Asp Leu Pro Gly Phe Pro Leu Val Arg Ser Cys Gln Met Pro Glu Cys
865                 870                 875                 880

Ser Lys Ile Lys Ser Glu Met Lys Thr Lys Leu Gly Glu Gln Gly Pro
                885                 890                 895

Gln Ile Leu Ser Val Gln Arg Val Tyr Ile Gln Thr Arg Glu Glu Lys
        900                 905                 910

Arg Ile Asn Leu Thr Ile Gly Ser Arg Ala Tyr Leu Leu Pro Asn Thr
    915                 920                 925

Ser Val Ile Ile Lys Cys Pro Val Arg Arg Phe Gln Lys Ser Leu Ile
930                 935                 940

Gln Trp Glu Lys Asp Gly Arg Cys Leu Gln Asn Ser Lys Arg Leu Gly
945                 950                 955                 960

Ile Thr Lys Ser Gly Ser Leu Lys Ile His Gly Leu Ala Ala Pro Asp
                965                 970                 975

Ile Gly Val Tyr Arg Cys Ile Ala Gly Ser Ala Gln Glu Thr Val Val
            980                 985                 990

Leu Lys Leu Ile Gly Thr Asp Asn Arg Leu Ile Ala Arg Pro Ala Leu
        995                 1000                1005

Arg Glu Pro Met Arg Glu Tyr Pro Gly Met Asp His Ser Glu Ala Asn
    1010                1015                1020

Ser Leu Gly Val Thr Trp His Lys Met Arg Gln Met Trp Asn Asn Lys
1025                1030                1035                1040

Asn Asp Leu Tyr Leu Asp Asp His Ile Ser Asn Gln Pro Phe Leu
                1045                1050                1055

Arg Ala Leu Leu Gly His Cys Ser Asn Ser Ala Gly Ser Thr Asn Ser
                1060                1065                1070

Trp Glu Leu Lys Asn Lys Gln Phe Glu Ala Ala Val Lys Gln Gly Ala
            1075                1080                1085

Tyr Ser Met Asp Thr Ala Gln Phe Asp Glu Leu Ile Arg Asn Met Ser
```

-continued

```
            1090                1095                1100
Gln Leu Met Glu Thr Gly Glu Val Ser Asp Asp Leu Ala Ser Gln Leu
1105                1110                1115                1120
Ile Tyr Gln Leu Val Ala Glu Leu Ala Lys Ala Gln Pro Thr His Met
                1125                1130                1135
Gln Trp Arg Gly Ile Gln Glu Glu Thr Pro Pro Ala Ala Gln Leu Arg
            1140                1145                1150
Gly Glu Thr Gly Ser Val Ser Gln Ser Ser His Ala Lys Asn Ser Gly
            1155                1160                1165
Lys Leu Thr Phe Lys Pro Lys Gly Pro Val Leu Met Arg Gln Ser Gln
            1170                1175                1180
Pro Pro Ser Ile Ser Phe Asn Lys Thr Ile Asn Ser Arg Ile Gly Asn
1185                1190                1195                1200
Thr Val Tyr Ile Thr Lys Arg Thr Glu Val Ile Asn Ile Leu Cys Asp
                1205                1210                1215
Leu Ile Thr Pro Ser Glu Ala Thr Tyr Thr Trp Thr Lys Asp Gly Thr
                1220                1225                1230
Leu Leu Gln Pro Ser Val Lys Ile Ile Leu Asp Gly Thr Gly Lys Ile
            1235                1240                1245
Gln Ile Gln Asn Pro Thr Arg Lys Glu Gln Gly Ile Tyr Glu Cys Ser
            1250                1255                1260
Val Ala Asn His Leu Gly Ser Asp Val Glu Ser Ser Val Leu Tyr
1265                1270                1275                1280
Ala Glu Ala Pro Val Ile Leu Ser Val Glu Arg Asn Ile Thr Lys Pro
                1285                1290                1295
Glu His Asn His Leu Ser Val Val Gly Gly Ile Val Glu Ala Ala
                1300                1305                1310
Leu Gly Ala Asn Val Thr Ile Arg Cys Pro Val Lys Gly Val Pro Gln
            1315                1320                1325
Pro Asn Ile Thr Trp Leu Lys Arg Gly Gly Ser Leu Ser Gly Asn Val
            1330                1335                1340
Ser Leu Leu Phe Asn Gly Ser Leu Leu Leu Gln Asn Val Ser Leu Glu
1345                1350                1355                1360
Asn Glu Gly Thr Tyr Val Cys Ile Ala Thr Asn Ala Leu Gly Lys Ala
                1365                1370                1375
Val Ala Thr Ser Val Leu His Leu Leu Glu Arg Arg Trp Pro Glu Ser
                1380                1385                1390
Arg Ile Val Phe Leu Gln Gly His Lys Lys Tyr Ile Leu Gln Ala Thr
            1395                1400                1405
Asn Thr Arg Thr Asn Ser Asn Asp Pro Thr Gly Glu Pro Pro Gln
            1410                1415                1420
Glu Pro Phe Trp Glu Pro Gly Asn Trp Ser His Cys Ser Ala Thr Cys
1425                1430                1435                1440
Gly His Leu Gly Ala Arg Ile Gln Arg Pro Gln Cys Val Met Ala Asn
                1445                1450                1455
Gly Gln Glu Val Ser Glu Ala Leu Cys Asp His Leu Gln Lys Pro Leu
            1460                1465                1470
Ala Gly Phe Glu Pro Cys Asn Ile Arg Asp Cys Pro Ala Arg Trp Phe
            1475                1480                1485
Thr Ser Val Trp Ser Gln Cys Ser Val Ser Cys Gly Glu Gly Tyr His
            1490                1495                1500
Ser Arg Gln Val Thr Cys Lys Arg Thr Lys Ala Asn Gly Thr Val Gln
1505                1510                1515                1520
```

-continued

```
Val Val Ser Pro Arg Ala Cys Ala Pro Lys Asp Arg Pro Leu Gly Arg
            1525                1530                1535
Lys Pro Cys Phe Gly His Pro Cys Val Gln Trp Glu Pro Gly Asn Arg
        1540                1545                1550
Cys Pro Gly Arg Cys Met Gly Arg Ala Val Arg Met Gln Gln Arg His
    1555                1560                1565
Thr Ala Cys Gln His Asn Ser Ser Asp Ser Asn Cys Asp Asp Arg Lys
    1570                1575                1580
Arg Pro Thr Leu Arg Arg Asn Cys Thr Ser Gly Ala Cys Asp Val Cys
1585                1590                1595                1600
Trp His Thr Gly Pro Trp Lys Pro Cys Thr Ala Ala Cys Gly Arg Gly
            1605                1610                1615
Phe Gln Ser Arg Lys Val Asp Cys Ile His Thr Arg Ser Cys Lys Pro
            1620                1625                1630
Val Ala Lys Arg His Cys Val Gln Lys Lys Pro Ile Ser Trp Arg
            1635                1640                1645
His Cys Leu Gly Pro Ser Cys Asp Arg Asp Cys Thr Asp Thr Thr His
        1650                1655                1660
Tyr Cys Met Phe Val Lys His Leu Asn Leu Cys Ser Leu Asp Arg Tyr
1665                1670                1675                1680
Lys Gln Arg Cys Cys Gln Ser Cys Gln Glu Gly
            1685                1690

<210> SEQ ID NO 3
<211> LENGTH: 1341
<212> TYPE: DNA
<213> ORGANISM: homo sapiens

<400> SEQUENCE: 3
atggcttcct ggacgagccc ctggtgggtg ctgatagggca tggtcttcat gcactctccc     60
ctcccgcaga ccacagctga gaaatctcct ggagcctatt ccttcccga gtttgcactt      120 tctcctcagg gaagttttct ggaagacaca acaggggagc agttcctcac ttatcgctat    180
gatgaccaga cctcaagaaa cactcgttca gatgaagaca agatggcaa ctgggatgct    240 tggggcgact ggagtgactg ctcccggacc tgtgggggag agcatcata ttctctgcgg    300 agatgtttga ctggaaggaa ttgtgaaggg cagaacattc ggtacaagac atgcagcaat    360
catgactgcc ctcagatgc agaagatttc agagcccagc agtgctcagc ctacaatgat    420
gtccagtatc agggcatta ctatgaatgg cttccacgat ataatgatcc tgctgccccg    480
tgtgcactca gtgtcatgc acaaggacaa aacttggtgg tggagctggc acctaaggta    540
ctggatggaa ctcgttgcaa cacggactcc ttggacatgt gtatcagtgg catctgtcag    600
gcagtgggct gcgatcggca actgggaagc aatgccaagg aggacaactg tggagtctgt    660
gccggcgatg gctccacctg caggcttgta cggggacaat caaagtcaca cgtttctcct    720
gaaaaaagag aagaaaatgt aattgctgtt cctttgggaa gtcgaagtgt gagaattaca    780
gtgaaaggac ctgcccacct ctttattgaa tcaaaaacac ttcaaggaag caaaggagaa    840
cacagcttta acagcccggg cgtctttgtc gtagaaaaca aacagtgga atttcagagg    900 ggctccgaga ggcaaacttt taagattcca ggacctctga tggctgattt catcttcaag    960
accaggtaca ctgcagccaa agacagcgtg gttcagttct tcttttacca gcccatcagt   1020
catcagtgga gacaaactga cttctttccc tgcactgtga cgtgtggagg aggttatcag   1080
ctcaattctg ctgaatgtgt ggatatccgc ttgaagaggg tagttcctga ccattattgt    1140
```

```
cactactacc ctgaaaatgt aaaaccaaaa ccaaaactga aggaatgcag catggatccc      1200
tgcccatcaa gtgatggatt taaagagata atgccctatg accacttcca acctcttcct      1260
cgagctggga acataatcct tggactgcat gttccgtgtc ctgtggagga gggattcaga      1320
gacggagctt tgtgtgtgta g                                                1341
```

<210> SEQ ID NO 4
<211> LENGTH: 446
<212> TYPE: PRT
<213> ORGANISM: homo sapiens

<400> SEQUENCE: 4

```
Met Ala Ser Trp Thr Ser Pro Trp Trp Val Leu Ile Gly Met Val Phe
 1               5                  10                  15

Met His Ser Pro Leu Pro Gln Thr Thr Ala Glu Lys Ser Pro Gly Ala
            20                  25                  30

Tyr Phe Leu Pro Glu Phe Ala Leu Ser Pro Gln Gly Ser Phe Leu Glu
        35                  40                  45

Asp Thr Thr Gly Glu Gln Phe Leu Thr Tyr Arg Tyr Asp Asp Gln Thr
    50                  55                  60

Ser Arg Asn Thr Arg Ser Asp Glu Asp Lys Asp Gly Asn Trp Asp Ala
65                  70                  75                  80

Trp Gly Asp Trp Ser Asp Cys Ser Arg Thr Cys Gly Gly Gly Ala Ser
                85                  90                  95

Tyr Ser Leu Arg Arg Cys Leu Thr Gly Arg Asn Cys Glu Gly Gln Asn
            100                 105                 110

Ile Arg Tyr Lys Thr Cys Ser Asn His Asp Cys Pro Pro Asp Ala Glu
        115                 120                 125

Asp Phe Arg Ala Gln Gln Cys Ser Ala Tyr Asn Asp Val Gln Tyr Gln
    130                 135                 140

Gly His Tyr Tyr Glu Trp Leu Pro Arg Tyr Asn Asp Pro Ala Ala Pro
145                 150                 155                 160

Cys Ala Leu Lys Cys His Ala Gln Gly Gln Asn Leu Val Val Glu Leu
                165                 170                 175

Ala Pro Lys Val Leu Asp Gly Thr Arg Cys Asn Thr Asp Ser Leu Asp
            180                 185                 190

Met Cys Ile Ser Gly Ile Cys Gln Ala Val Gly Cys Asp Arg Gln Leu
        195                 200                 205

Gly Ser Asn Ala Lys Glu Asp Asn Cys Gly Val Cys Ala Gly Asp Gly
    210                 215                 220

Ser Thr Cys Arg Leu Val Arg Gly Gln Ser Lys Ser His Val Ser Pro
225                 230                 235                 240

Glu Lys Arg Glu Glu Asn Val Ile Ala Val Pro Leu Gly Ser Arg Ser
                245                 250                 255

Val Arg Ile Thr Val Lys Gly Pro Ala His Leu Phe Ile Glu Ser Lys
            260                 265                 270

Thr Leu Gln Gly Ser Lys Gly Glu His Ser Phe Asn Ser Pro Gly Val
        275                 280                 285

Phe Val Val Glu Asn Thr Thr Val Glu Phe Gln Arg Gly Ser Glu Arg
    290                 295                 300

Gln Thr Phe Lys Ile Pro Gly Pro Leu Met Ala Asp Phe Ile Phe Lys
305                 310                 315                 320

Thr Arg Tyr Thr Ala Ala Lys Asp Ser Val Val Gln Phe Phe Tyr
                325                 330                 335
```

```
Gln Pro Ile Ser His Gln Trp Arg Gln Thr Asp Phe Phe Pro Cys Thr
            340                 345                 350
Val Thr Cys Gly Gly Gly Tyr Gln Leu Asn Ser Ala Glu Cys Val Asp
            355                 360                 365
Ile Arg Leu Lys Arg Val Val Pro Asp His Tyr Cys His Tyr Tyr Pro
            370                 375                 380
Glu Asn Val Lys Pro Lys Pro Lys Leu Lys Glu Cys Ser Met Asp Pro
385                 390                 395                 400
Cys Pro Ser Ser Asp Gly Phe Lys Glu Ile Met Pro Tyr Asp His Phe
                405                 410                 415
Gln Pro Leu Pro Arg Ala Gly Asn Ile Ile Leu Gly Leu His Val Pro
            420                 425                 430
Cys Pro Val Glu Glu Gly Phe Arg Asp Gly Ala Leu Cys Val
            435                 440                 445

<210> SEQ ID NO 5
<211> LENGTH: 1119
<212> TYPE: DNA
<213> ORGANISM: homo sapiens

<400> SEQUENCE: 5
atggcttcct ggacgagccc ctggtgggtg ctgataggga tggtcttcat gcactctccc     60
ctcccgcaga ccacagctga gaaatctcct ggaaggaatt gtgaagggca gaacattcgg    120
tacaagacat gcagcaatca tgactgccct ccagatgcag aagatttcag agcccagcag    180
tgctcagcct acaatgatgt ccagtatcag gggcattact atgaatggct tccacgatat    240
aatgatcctg ctgccccgtg tgcactcaag tgtcatgcac aaggacaaaa cttggtggtg    300
gagctggcac ctaaggtact ggatggaact cgttgcaaca cggactcctt ggacatgtgt    360
atcagtggca tctgtcaggc agtgggctgc gatcggcaac tgggaagcaa tgccaaggag    420
gacaactgtg gagtctgtgc cggcgatggc tccacctgca ggcttgtacg gggacaatca    480
aagtcacacg tttctcctga aaaagagaaa gaaaatgtaa ttgctgttcc tttgggaagt    540
cgaagtgtga gaattacagt gaaaggacct gcccacctct ttattgaatc aaaaacactt    600
caaggaagca aggagaaaca cagctttaac agccccggcg tctttgtcgt agaaaacaca    660
acagtggaat tcagaggggc tccgagaggc aaacttttta gattccagg acctctgatg    720 gctgatttca tcttcaagac caggtacact gcagccaaag acagcgtggt tcagttcttc    780
ttttaccagc ccatcagtca tcagtggaga caaactgact tctttccctg cactgtgacg    840
tgtggaggag gttatcagct caattctgct gaatgtgtgg atatccgctt gaagagggta    900
gttcctgacc attattgtca ctactaccct gaaaatgtaa aaccaaaacc aaaactgaag    960
gaatgcagca tggatccctg cccatcaagt gatggattta agagataat gccctatgac   1020 cacttccaac tcttcctcg agctgggaac ataatccttg gactgcatgt tccgtgtcct   1080
gtggaggagg gattcagaga cggagctttg tgtgtgtag                          1119

<210> SEQ ID NO 6
<211> LENGTH: 372
<212> TYPE: PRT
<213> ORGANISM: homo sapiens

<400> SEQUENCE: 6

Met Ala Ser Trp Thr Ser Pro Trp Trp Val Leu Ile Gly Met Val Phe
 1               5                  10                  15
```

```
Met His Ser Pro Leu Pro Gln Thr Thr Ala Glu Lys Ser Pro Gly Arg
            20                  25                  30
Asn Cys Glu Gly Gln Asn Ile Arg Tyr Lys Thr Cys Ser Asn His Asp
            35                  40                  45
Cys Pro Pro Asp Ala Glu Asp Phe Arg Ala Gln Gln Cys Ser Ala Tyr
            50                  55                  60
Asn Asp Val Gln Tyr Gln Gly His Tyr Tyr Glu Trp Leu Pro Arg Tyr
 65                  70                  75                  80
Asn Asp Pro Ala Ala Pro Cys Ala Leu Lys Cys His Ala Gln Gly Gln
                 85                  90                  95
Asn Leu Val Val Glu Leu Ala Pro Lys Val Leu Asp Gly Thr Arg Cys
            100                 105                 110
Asn Thr Asp Ser Leu Asp Met Cys Ile Ser Gly Ile Cys Gln Ala Val
            115                 120                 125
Gly Cys Asp Arg Gln Leu Gly Ser Asn Ala Lys Glu Asp Asn Cys Gly
130                 135                 140
Val Cys Ala Gly Asp Gly Ser Thr Cys Arg Leu Val Arg Gly Gln Ser
145                 150                 155                 160
Lys Ser His Val Ser Pro Glu Lys Arg Glu Glu Asn Val Ile Ala Val
            165                 170                 175
Pro Leu Gly Ser Arg Ser Val Arg Ile Thr Val Lys Gly Pro Ala His
            180                 185                 190
Leu Phe Ile Glu Ser Lys Thr Leu Gln Gly Ser Lys Gly Glu His Ser
            195                 200                 205
Phe Asn Ser Pro Gly Val Phe Val Glu Asn Thr Thr Val Glu Phe
            210                 215                 220
Gln Arg Gly Ser Glu Arg Gln Thr Phe Lys Ile Pro Gly Pro Leu Met
225                 230                 235                 240
Ala Asp Phe Ile Phe Lys Thr Arg Tyr Thr Ala Ala Lys Asp Ser Val
            245                 250                 255
Val Gln Phe Phe Phe Tyr Gln Pro Ile Ser His Gln Trp Arg Gln Thr
            260                 265                 270
Asp Phe Phe Pro Cys Thr Val Thr Cys Gly Gly Gly Tyr Gln Leu Asn
            275                 280                 285
Ser Ala Glu Cys Val Asp Ile Arg Leu Lys Arg Val Pro Asp His
            290                 295                 300
Tyr Cys His Tyr Tyr Pro Glu Asn Val Lys Pro Lys Pro Lys Leu Lys
305                 310                 315                 320
Glu Cys Ser Met Asp Pro Cys Pro Ser Ser Asp Gly Phe Lys Glu Ile
                325                 330                 335
Met Pro Tyr Asp His Phe Gln Pro Leu Pro Arg Ala Gly Asn Ile Ile
            340                 345                 350
Leu Gly Leu His Val Pro Cys Pro Val Glu Glu Gly Phe Arg Asp Gly
            355                 360                 365
Ala Leu Cys Val
    370
```

<210> SEQ ID NO 7
<211> LENGTH: 2175
<212> TYPE: DNA
<213> ORGANISM: homo sapiens

<400> SEQUENCE: 7
atggcttcct ggacgagccc ctggtgggtg ctgataggga tggtcttcat gcactctccc        60

-continued

| | |
|---|---|
| ctcccgcaga ccacagctga gaaatctcct ggagcctatt tccttcccga gtttgcactt | 120 |
| tctcctcagg gaagttttct ggaagacaca acagggagc agttcctcac ttatcgctat | 180 |
| gatgaccaga cctcaagaaa cactcgttca gatgaagaca agatggcaa ctgggatgct | 240 |
| tggggcgact ggagtgactg ctcccggacc tgtgggggag gagcatcata ttctctgcgg | 300 |
| agatgtttga ctggaaggaa ttgtgaaggg cagaacattc ggtacaagac atgcagcaat | 360 |
| catgactgcc ctccagatgc agaagatttc agagcccagc agtgctcagc ctacaatgat | 420 |
| gtccagtatc aggggcatta ctatgaatgg cttccacgat ataatgatcc tgctgccccg | 480 |
| tgtgcactca agtgtcatgc acaaggacaa aacttggtgg tggagctggc acctaaggta | 540 |
| ctggatggaa ctcgttgcaa cacggactcc ttggacatgt gtatcagtgg catctgtcag | 600 |
| gcagtgggct gcgatcggca actgggaagc aatgccaagg aggacaactg tggagtctgt | 660 |
| gccggcgatg gctccacctg caggcttgta cggggacaat caaagtcaca cgtttctcct | 720 |
| gaaaaagag aagaaaatgt aattgctgtt cctttgggaa gtcgaagtgt gagaattaca | 780 |
| gtgaaggac ctgcccacct ctttattgaa tcaaaaacac ttcaaggaag caaggagaa | 840 |
| cacagcttta acagccccgg cgtctttgtc gtagaaaaca acagtggaa atttcagagg | 900 |
| ggctccgaga ggcaaacttt taagattcca ggacctctga tggctgattt catcttcaag | 960 |
| accaggtaca ctgcagccaa agacagcgtg gttcagttct tcttttacca gcccatcagt | 1020 |
| catcagtgga gacaaactga cttctttccc tgcactgtga cgtgtggagg aggttatcag | 1080 |
| ctcaattctg ctgaatgtgt ggatatccgc ttgaagaggg tagttcctga ccattattgt | 1140 |
| cactactacc ctgaaaatgt aaaaccaaaa ccaaaactga aggaatgcag catggatccc | 1200 |
| tgcccatcaa gtgatggatt taaagagata atgcccctatg accacttcca acctcttcct | 1260 |
| cgctgggaac ataatccttg gactgcatgt tccgtgtcct gtggaggagg gattcagaga | 1320 |
| cggagctttg tgtgtgtaga ggaatccatg catggagaga tattgcaggt ggaagaatgg | 1380 |
| aagtgcatgt acgcacccaa acccaaggtt atgcaaactt gtaatctgtt tgattgcccc | 1440 |
| aagtggatt ccatggagtg gtctcagtgc acagtgactt gtggccgagg gttacggtac | 1500 |
| cgggttgttc tgtgtattaa ccaccgcgga gagcatgttg ggggctgcaa tccacaactg | 1560 |
| aagttacaca tcaagaagaa atgtgtcatt cccatcccgt gttataaacc aaaagaaaaa | 1620 |
| agtccagtgg aagcaaaatt gccttggctg aaacaagcac aagaactaga agagaccaga | 1680 |
| atagcaacag aagaaccaac gttcattcca gaaccctggt cagcctgcag taccacgtgt | 1740 |
| gggccaggtg tgcaggtccg cgaggtgaag tgccgtgtgc tcctcacatt cacgcagact | 1800 |
| gagactgagc tgcccgagga agagtgtgaa ggccccaagc tgcccaccga acggccctgc | 1860 |
| ctcctggaag catgtgatga gagcccggcc tcccgagagc tagacatccc tctccctgag | 1920 |
| gacagtgaga cgacttacga ctgggagtac gctgggttca ccccttgcac agcaacatgc | 1980 |
| ttgggaggcc atcaagaagc catagcagtg tgcttacata tccagaccca gcagacagtc | 2040 |
| aatgacagct tgtgtgatat ggtccaccgt cctccagcca tgagccaggc ctgtaacaca | 2100 |
| gagccctgtc cccccaggag agagccagca gcttgtagaa gcatgccggg ttacataatg | 2160 |
| gtcctgctag tctga | 2175 |

<210> SEQ ID NO 8
<211> LENGTH: 724
<212> TYPE: PRT
<213> ORGANISM: homo sapiens

<400> SEQUENCE: 8

-continued

```
Met Ala Ser Trp Thr Ser Pro Trp Trp Val Leu Ile Gly Met Val Phe
 1               5                   10                  15

Met His Ser Pro Leu Pro Gln Thr Thr Ala Glu Lys Ser Pro Gly Ala
                20                  25                  30

Tyr Phe Leu Pro Glu Phe Ala Leu Ser Pro Gln Gly Ser Phe Leu Glu
            35                  40                  45

Asp Thr Thr Gly Glu Gln Phe Leu Thr Tyr Arg Tyr Asp Asp Gln Thr
        50                  55                  60

Ser Arg Asn Thr Arg Ser Asp Glu Asp Lys Asp Gly Asn Trp Asp Ala
65                  70                  75                  80

Trp Gly Asp Trp Ser Asp Cys Ser Arg Thr Cys Gly Gly Ala Ser
                85                  90                  95

Tyr Ser Leu Arg Arg Cys Leu Thr Gly Arg Asn Cys Glu Gly Gln Asn
                100                 105                 110

Ile Arg Tyr Lys Thr Cys Ser Asn His Asp Cys Pro Pro Asp Ala Glu
            115                 120                 125

Asp Phe Arg Ala Gln Gln Cys Ser Ala Tyr Asn Asp Val Gln Tyr Gln
        130                 135                 140

Gly His Tyr Tyr Glu Trp Leu Pro Arg Tyr Asn Asp Pro Ala Ala Pro
145                 150                 155                 160

Cys Ala Leu Lys Cys His Ala Gln Gly Gln Asn Leu Val Val Glu Leu
                165                 170                 175

Ala Pro Lys Val Leu Asp Gly Thr Arg Cys Asn Thr Asp Ser Leu Asp
                180                 185                 190

Met Cys Ile Ser Gly Ile Cys Gln Ala Val Gly Cys Asp Arg Gln Leu
            195                 200                 205

Gly Ser Asn Ala Lys Glu Asp Asn Cys Gly Val Cys Ala Gly Asp Gly
210                 215                 220

Ser Thr Cys Arg Leu Val Arg Gly Gln Ser Lys Ser His Val Ser Pro
225                 230                 235                 240

Glu Lys Arg Glu Glu Asn Val Ile Ala Val Pro Leu Gly Ser Arg Ser
                245                 250                 255

Val Arg Ile Thr Val Lys Gly Pro Ala His Leu Phe Ile Glu Ser Lys
                260                 265                 270

Thr Leu Gln Gly Ser Lys Gly Glu His Ser Phe Asn Ser Pro Gly Val
            275                 280                 285

Phe Val Val Glu Asn Thr Thr Val Glu Phe Gln Arg Gly Ser Glu Arg
        290                 295                 300

Gln Thr Phe Lys Ile Pro Gly Pro Leu Met Ala Asp Phe Ile Phe Lys
305                 310                 315                 320

Thr Arg Tyr Thr Ala Ala Lys Asp Ser Val Val Gln Phe Phe Phe Tyr
                325                 330                 335

Gln Pro Ile Ser His Gln Trp Arg Gln Thr Asp Phe Phe Pro Cys Thr
                340                 345                 350

Val Thr Cys Gly Gly Gly Tyr Gln Leu Asn Ser Ala Glu Cys Val Asp
            355                 360                 365

Ile Arg Leu Lys Arg Val Val Pro Asp His Tyr Cys His Tyr Tyr Pro
        370                 375                 380

Glu Asn Val Lys Pro Lys Pro Lys Leu Lys Glu Cys Ser Met Asp Pro
385                 390                 395                 400

Cys Pro Ser Ser Asp Gly Phe Lys Glu Ile Met Pro Tyr Asp His Phe
                405                 410                 415
```

```
Gln Pro Leu Pro Arg Trp Glu His Asn Pro Trp Thr Ala Cys Ser Val
            420                 425                 430
Ser Cys Gly Gly Gly Ile Gln Arg Arg Ser Phe Val Cys Val Glu Glu
        435                 440                 445
Ser Met His Gly Glu Ile Leu Gln Val Glu Glu Trp Lys Cys Met Tyr
    450                 455                 460
Ala Pro Lys Pro Lys Val Met Gln Thr Cys Asn Leu Phe Asp Cys Pro
465                 470                 475                 480
Lys Trp Ile Ala Met Glu Trp Ser Gln Cys Thr Val Thr Cys Gly Arg
                485                 490                 495
Gly Leu Arg Tyr Arg Val Val Leu Cys Ile Asn His Arg Gly Glu His
            500                 505                 510
Val Gly Gly Cys Asn Pro Gln Leu Lys Leu His Ile Lys Glu Glu Cys
        515                 520                 525
Val Ile Pro Ile Pro Cys Tyr Lys Pro Lys Glu Lys Ser Pro Val Glu
    530                 535                 540
Ala Lys Leu Pro Trp Leu Lys Gln Ala Gln Glu Leu Glu Glu Thr Arg
545                 550                 555                 560
Ile Ala Thr Glu Glu Pro Thr Phe Ile Pro Glu Pro Trp Ser Ala Cys
                565                 570                 575
Ser Thr Thr Cys Gly Pro Gly Val Gln Val Arg Glu Val Lys Cys Arg
            580                 585                 590
Val Leu Leu Thr Phe Thr Gln Thr Glu Thr Glu Leu Pro Glu Glu Glu
        595                 600                 605
Cys Glu Gly Pro Lys Leu Pro Thr Glu Arg Pro Cys Leu Leu Glu Ala
    610                 615                 620
Cys Asp Glu Ser Pro Ala Ser Arg Glu Leu Asp Ile Pro Leu Pro Glu
625                 630                 635                 640
Asp Ser Glu Thr Thr Tyr Asp Trp Glu Tyr Ala Gly Phe Thr Pro Cys
                645                 650                 655
Thr Ala Thr Cys Leu Gly Gly His Gln Glu Ala Ile Ala Val Cys Leu
            660                 665                 670
His Ile Gln Thr Gln Gln Thr Val Asn Asp Ser Leu Cys Asp Met Val
        675                 680                 685
His Arg Pro Pro Ala Met Ser Gln Ala Cys Asn Thr Glu Pro Cys Pro
    690                 695                 700
Pro Arg Arg Glu Pro Ala Ala Cys Arg Ser Met Pro Gly Tyr Ile Met
705                 710                 715                 720
Val Leu Leu Val

<210> SEQ ID NO 9
<211> LENGTH: 1953
<212> TYPE: DNA
<213> ORGANISM: homo sapiens

<400> SEQUENCE: 9
atggcttcct ggacgagccc ctggtgggtg ctgatagggc tggtcttcat gcactctccc      60
ctcccgcaga ccacagctga aaatctcct ggaaggaatt gtgaaggca gaacattcgg      120 tacaagacat gcagcaatca tgactgccct ccagatgcag aagatttcag agcccagcag    180
tgctcagcct acaatgatgt ccagtatcag gggcattact atgaatggct tccacgatat    240
aatgatcctg ctgccccgtg tgcactcaag tgtcatgcac aaggacaaaa cttggtggtg    300
gagctggcac ctaaggtact ggatggaact cgttgcaaca cggactcctt ggacatgtgt    360
```

-continued

```
atcagtggca tctgtcaggc agtgggctgc gatcggcaac tgggaagcaa tgccaaggag      420
gacaactgtg gagtctgtgc cggcgatggc tccacctgca ggcttgtacg gggacaatca      480
aagtcacacg tttctcctga aaaagagaaa gaaaatgtaa ttgctgttcc tttgggaagt      540
cgaagtgtga gaattacagt gaaggacctg cccacctct ttattgaatc aaaaacactt       600
caaggaagca aggagaaca cagctttaac agccccggcg tctttgtcgt agaaaacaca       660
acagtggaat tcagaggggg ctccgagagg caaactttta agattccagg acctctgatg      720
gctgatttca tcttcaagac caggtacact gcagccaaag acagcgtggt tcagttcttc      780
ttttaccagc ccatcagtca tcagtggaga caaactgact tctttccctg cactgtgacg      840
tgtggaggag gttatcagct caattctgct gaatgtgtgg atatccgctt gaagagggta      900
gttcctgacc attattgtca ctactaccct gaaaatgtaa aaccaaaacc aaaactgaag      960
gaatgcagca tggatccctg cccatcaagt gatggattta agagataat gccctatgac     1020 cacttccaac ctcttcctcg ctgggaacat aatccttgga ctgcatgttc cgtgtcctgt     1080
ggaggaggga ttcagagacg gagctttgtg tgtgtagagg aatccatgca tggagagata     1140
ttgcaggtgg aagaatggaa gtgcatgtac gcacccaaac ccaaggttat gcaaacttgt     1200
aatctgtttg attgccccaa gtggattgcc atggagtggt ctcagtgcac agtgacttgt     1260
ggccgagggt tacggtaccg ggttgttctg tgtattaacc accgcggaga gcatgttggg     1320
ggctgcaatc acaactgaa gttacacatc aagaagaat gtgtcattcc catcccgtgt      1380
tataaaccaa agaaaaaag tccagtggaa gcaaaattgc cttggctgaa caagcacaa      1440 gaactagaag agaccagaat agcaacagaa gaaccaacgt tcattccaga accctggtca     1500
gcctgcagta ccacgtgtgg gccaggtgtg caggtccgcg aggtgaagtg ccgtgtgctc     1560
ctcacattca cgcagactga gactgagctg cccgaggaag agtgtgaagg ccccaagctg     1620
cccaccgaac ggccctgcct cctggaagca tgtgatgaga gccggcctc ccgagagcta     1680 gacatccctc tccctgagga cagtgagacg acttacgact gggagtacgc tgggttcacc     1740
ccttgcacag caacatgctt gggaggccat caagaagcca tagcagtgtg cttacatatc     1800
cagacccagc agacagtcaa tgacagcttg tgtgatatgg tccaccgtcc tccagccatg     1860
agccaggcct gtaacacaga gccctgtccc cccaggagag agccagcagc ttgtagaagc     1920
atgccgggtt acataatggt cctgctagtc tga                                 1953
```

<210> SEQ ID NO 10
<211> LENGTH: 650
<212> TYPE: PRT
<213> ORGANISM: homo sapiens

<400> SEQUENCE: 10

```
Met Ala Ser Trp Thr Ser Pro Trp Trp Val Leu Ile Gly Met Val Phe
 1               5                  10                  15

Met His Ser Pro Leu Pro Gln Thr Thr Ala Glu Lys Ser Pro Gly Arg
            20                  25                  30

Asn Cys Glu Gly Gln Asn Ile Arg Tyr Lys Thr Cys Ser Asn His Asp
        35                  40                  45

Cys Pro Pro Asp Ala Glu Asp Phe Arg Ala Gln Cys Ser Ala Tyr
    50                  55                  60

Asn Asp Val Gln Tyr Gln Gly His Tyr Tyr Glu Trp Leu Pro Arg Tyr
65                  70                  75                  80

Asn Asp Pro Ala Ala Pro Cys Ala Leu Lys Cys His Ala Gln Gly Gln
                85                  90                  95
```

```
Asn Leu Val Val Glu Leu Ala Pro Lys Val Leu Asp Gly Thr Arg Cys
            100                 105                 110

Asn Thr Asp Ser Leu Asp Met Cys Ile Ser Gly Ile Cys Gln Ala Val
        115                 120                 125

Gly Cys Asp Arg Gln Leu Gly Ser Asn Ala Lys Glu Asp Asn Cys Gly
    130                 135                 140

Val Cys Ala Gly Asp Gly Ser Thr Cys Arg Leu Val Arg Gly Gln Ser
145                 150                 155                 160

Lys Ser His Val Ser Pro Glu Lys Arg Glu Asn Val Ile Ala Val
                165                 170                 175

Pro Leu Gly Ser Arg Ser Val Arg Ile Thr Val Lys Gly Pro Ala His
            180                 185                 190

Leu Phe Ile Glu Ser Lys Thr Leu Gln Gly Ser Lys Gly Glu His Ser
        195                 200                 205

Phe Asn Ser Pro Gly Val Phe Val Val Glu Asn Thr Thr Val Glu Phe
    210                 215                 220

Gln Arg Gly Ser Glu Arg Gln Thr Phe Lys Ile Pro Gly Pro Leu Met
225                 230                 235                 240

Ala Asp Phe Ile Phe Lys Thr Arg Tyr Thr Ala Ala Lys Asp Ser Val
                245                 250                 255

Val Gln Phe Phe Phe Tyr Gln Pro Ile Ser His Gln Trp Arg Gln Thr
            260                 265                 270

Asp Phe Phe Pro Cys Thr Val Cys Gly Gly Tyr Gln Leu Asn
        275                 280                 285

Ser Ala Glu Cys Val Asp Ile Arg Leu Lys Arg Val Val Pro Asp His
    290                 295                 300

Tyr Cys His Tyr Tyr Pro Glu Asn Val Lys Pro Lys Pro Lys Leu Lys
305                 310                 315                 320

Glu Cys Ser Met Asp Pro Cys Pro Ser Ser Asp Gly Phe Lys Glu Ile
                325                 330                 335

Met Pro Tyr Asp His Phe Gln Pro Leu Pro Arg Trp Glu His Asn Pro
            340                 345                 350

Trp Thr Ala Cys Ser Val Ser Cys Gly Gly Gly Ile Gln Arg Arg Ser
        355                 360                 365

Phe Val Cys Val Glu Glu Ser Met His Gly Glu Ile Leu Gln Val Glu
    370                 375                 380

Glu Trp Lys Cys Met Tyr Ala Pro Lys Pro Lys Val Met Gln Thr Cys
385                 390                 395                 400

Asn Leu Phe Asp Cys Pro Lys Trp Ile Ala Met Glu Trp Ser Gln Cys
                405                 410                 415

Thr Val Thr Cys Gly Arg Gly Leu Arg Tyr Arg Val Val Leu Cys Ile
            420                 425                 430

Asn His Arg Gly Glu His Val Gly Cys Asn Pro Gln Leu Lys Leu
        435                 440                 445

His Ile Lys Glu Glu Cys Val Ile Pro Ile Pro Cys Tyr Lys Pro Lys
    450                 455                 460

Glu Lys Ser Pro Val Glu Ala Lys Leu Pro Trp Leu Lys Gln Ala Gln
465                 470                 475                 480

Glu Leu Glu Glu Thr Arg Ile Ala Thr Glu Glu Pro Thr Phe Ile Pro
                485                 490                 495

Glu Pro Trp Ser Ala Cys Ser Thr Thr Cys Gly Pro Gly Val Gln Val
            500                 505                 510
```

```
Arg Glu Val Lys Cys Arg Val Leu Leu Thr Phe Thr Gln Thr Glu Thr
            515                 520                 525
Glu Leu Pro Glu Glu Cys Glu Gly Pro Lys Leu Pro Thr Glu Arg
        530                 535                 540
Pro Cys Leu Leu Glu Ala Cys Asp Glu Ser Pro Ala Ser Arg Glu Leu
545                 550                 555                 560
Asp Ile Pro Leu Pro Glu Asp Ser Glu Thr Thr Tyr Asp Trp Glu Tyr
                565                 570                 575
Ala Gly Phe Thr Pro Cys Thr Ala Thr Cys Leu Gly Gly His Gln Glu
            580                 585                 590
Ala Ile Ala Val Cys Leu His Ile Gln Thr Gln Gln Thr Val Asn Asp
            595                 600                 605
Ser Leu Cys Asp Met Val His Arg Pro Pro Ala Met Ser Gln Ala Cys
        610                 615                 620
Asn Thr Glu Pro Cys Pro Pro Arg Arg Glu Pro Ala Ala Cys Arg Ser
625                 630                 635                 640
Met Pro Gly Tyr Ile Met Val Leu Leu Val
                645                 650

<210> SEQ ID NO 11
<211> LENGTH: 2538
<212> TYPE: DNA
<213> ORGANISM: homo sapiens

<400> SEQUENCE: 11
atggcttcct ggacgagccc ctggtgggtg ctgataggga tggtcttcat gcactctccc      60
ctcccgcaga ccacagctga gaaatctcct ggagcctatt ccttcccga gtttgcactt     120
tctcctcagg gaagttttct ggaagacaca acagggagc agttcctcac ttatcgctat     180
gatgaccaga cctcaagaaa cactcgttca gatgaagaca agatggcaa ctgggatgct     240
tgggcgact ggagtgactg ctcccggacc tgtgggggag gagcatcata ttctctgcgg     300
agatgtttga ctggaaggaa ttgtgaaggg cagaacattc ggtacaagac atgcagcaat     360
catgactgcc ctccagatgc agaagatttc agagcccagc agtgctcagc ctacaatgat     420
gtccagtatc aggggcatta ctatgaatgg cttccacgat ataatgatcc tgctgccccg     480
tgtgcactca gtgtcatgc acaaggacaa acttggtgg tggagctggc acctaaggta     540
ctggatggaa ctcgttgcaa cacggactcc ttggacatgt gtatcagtgg catctgtcag     600
gcagtgggct gcgatcggca actgggaagc aatgccaagg aggacaactg tggagtctgt     660
gccggcgatg ctccacctg caggcttgta cggggacaat caaagtcaca cgtttctcct     720
gaaaaaagag aagaaaatgt aattgctgtt cctttggaa gtcgaagtgt gagaattaca     780
gtgaaaggac ctgcccacct ctttattgaa tcaaaacac ttcaaggaag caaggagaa     840
cacagcttta cagccccgg cgtctttgtc gtagaaaaca caacagtgga atttcagagg     900
ggctccgaga ggcaaacttt taagattcca ggacctctga tggctgattt catcttcaag     960
accaggtaca ctgcagccaa agacagcgtg gttcagttct tcttttacca gcccatcagt    1020
catcagtgga gacaaactga cttctttccc tgcactgtga cgtgtggagg aggttatcag    1080
ctcaattctg ctgaatgtgt ggatatccgc ttgaagaggg tagttcctga ccattattgt    1140
cactactacc ctgaaaatgt aaaaccaaaa ccaaaactga aggaatgcag catggatccc    1200
tgcccatcaa gtgatggatt taagagata atgcctatg accacttcca acctcttcct    1260
cgctgggaac ataatccttg gactgcatgt tccgtgtcct gtgaggagg gattcagaga    1320
```

-continued

```
cggagctttg tgtgtgtaga ggaatccatg catggagaga tattgcaggt ggaagaatgg      1380
aagtgcatgt acgcacccaa acccaaggtt atgcaaactt gtaatctgtt tgattgcccc      1440
aagtggattg ccatggagtg gtctcagtgc acagtgactt gtggccgagg gttacggtac      1500
cgggttgttc tgtgtattaa ccaccgcgga gagcatgttg ggggctgcaa tccacaactg      1560
aagttacaca tcaagaaga atgtgtcatt cccatcccgt gttataaacc aaaagaaaaa       1620
agtccagtgg aagcaaaatt gccttggctg aaacaagcac aagaactaga agagaccaga     1680
atagcaacag aagaaccaac gttcattcca gaaccctggt cagcctgcag taccacgtgt      1740
gggccaggtg tgcaggtccg cgaggtgaag tgccgtgtgc tcctcacatt cacgcagact      1800
gagactgagc tgcccgagga agagtgtgaa ggccccaagc tgcccaccga acggccctgc     1860
ctcctggaag catgtgatga gagcccggcc tcccgagagc tagacatccc tctccctgag     1920
gacagtgaga cgacttacga ctgggagtac gctgggttca ccccttgcac agcaacatgc     1980
ttgggaggcc atcaagaagc catagcagtg tgcttacata tccagaccca gcagacagtc     2040
aatgacagct tgtgtgatat ggtccaccgt cctccagcca tgagccaggc ctgtaacaca     2100
gagccctgtc ccccaggtg gcatgtgggc tcttggggc cctgctcagc tacctgtgga       2160
gttggaattc agaccgaga tgtgtactgc ctgcacccag gggagacccc tgcccctcct       2220
gaggagtgcc gagatgaaaa gccccatgct ttacaagcat gcaatcagtt tgactgcccc     2280
cctggctggc acattgaaga atggcagcag tgttccagga cttgtggcgg gggaactcag     2340
aacagaagag tcacctgtcg gcagctgcta acggatggca gctttttgaa tctctcagat     2400
gaattgtgcc aaggacccaa ggcatcgtct cacaagtcct gtgccaggac agactgtcct     2460
ccacatttag ctgtgggaga ctggtcgaag gagcattcaa tgcaagagga caatggagca    2520
ggatctacac aattctaa                                                    2538
```

<210> SEQ ID NO 12
<211> LENGTH: 845
<212> TYPE: PRT
<213> ORGANISM: homo sapiens

<400> SEQUENCE: 12

```
Met Ala Ser Trp Thr Ser Pro Trp Trp Val Leu Ile Gly Met Val Phe
  1               5                  10                  15

Met His Ser Pro Leu Pro Gln Thr Thr Ala Glu Lys Ser Pro Gly Ala
                 20                  25                  30

Tyr Phe Leu Pro Glu Phe Ala Leu Ser Pro Gln Gly Ser Phe Leu Glu
             35                  40                  45

Asp Thr Thr Gly Glu Gln Phe Leu Thr Tyr Arg Tyr Asp Asp Gln Thr
         50                  55                  60

Ser Arg Asn Thr Arg Ser Asp Glu Asp Lys Asp Gly Asn Trp Asp Ala
 65                  70                  75                  80

Trp Gly Asp Trp Ser Asp Cys Ser Arg Thr Cys Gly Gly Gly Ala Ser
                 85                  90                  95

Tyr Ser Leu Arg Arg Cys Leu Thr Gly Arg Asn Cys Glu Gly Gln Asn
            100                 105                 110

Ile Arg Tyr Lys Thr Cys Ser Asn His Asp Cys Pro Pro Asp Ala Glu
        115                 120                 125

Asp Phe Arg Ala Gln Gln Cys Ser Ala Tyr Asn Asp Val Gln Tyr Gln
    130                 135                 140

Gly His Tyr Tyr Glu Trp Leu Pro Arg Tyr Asn Asp Pro Ala Ala Pro
145                 150                 155                 160
```

-continued

```
Cys Ala Leu Lys Cys His Ala Gln Gly Gln Asn Leu Val Val Glu Leu
                165                 170                 175
Ala Pro Lys Val Leu Asp Gly Thr Arg Cys Asn Thr Asp Ser Leu Asp
            180                 185                 190
Met Cys Ile Ser Gly Ile Cys Gln Ala Val Gly Cys Asp Arg Gln Leu
        195                 200                 205
Gly Ser Asn Ala Lys Glu Asp Asn Cys Gly Val Cys Ala Gly Asp Gly
    210                 215                 220
Ser Thr Cys Arg Leu Val Arg Gly Gln Ser Lys Ser His Val Ser Pro
225                 230                 235                 240
Glu Lys Arg Glu Glu Asn Val Ile Ala Val Pro Leu Gly Ser Arg Ser
                245                 250                 255
Val Arg Ile Thr Val Lys Gly Pro Ala His Leu Phe Ile Glu Ser Lys
            260                 265                 270
Thr Leu Gln Gly Ser Lys Gly Glu His Ser Phe Asn Ser Pro Gly Val
        275                 280                 285
Phe Val Val Glu Asn Thr Thr Val Glu Phe Gln Arg Gly Ser Glu Arg
    290                 295                 300
Gln Thr Phe Lys Ile Pro Gly Pro Leu Met Ala Asp Phe Ile Phe Lys
305                 310                 315                 320
Thr Arg Tyr Thr Ala Ala Lys Asp Ser Val Val Gln Phe Phe Phe Tyr
                325                 330                 335
Gln Pro Ile Ser His Gln Trp Arg Gln Thr Asp Phe Phe Pro Cys Thr
            340                 345                 350
Val Thr Cys Gly Gly Gly Tyr Gln Leu Asn Ser Ala Glu Cys Val Asp
        355                 360                 365
Ile Arg Leu Lys Arg Val Val Pro Asp His Tyr Cys His Tyr Tyr Pro
    370                 375                 380
Glu Asn Val Lys Pro Lys Pro Lys Leu Lys Glu Cys Ser Met Asp Pro
385                 390                 395                 400
Cys Pro Ser Ser Asp Gly Phe Lys Glu Ile Met Pro Tyr Asp His Phe
                405                 410                 415
Gln Pro Leu Pro Arg Trp Glu His Asn Pro Trp Thr Ala Cys Ser Val
            420                 425                 430
Ser Cys Gly Gly Gly Ile Gln Arg Arg Ser Phe Val Cys Val Glu Glu
        435                 440                 445
Ser Met His Gly Glu Ile Leu Gln Val Glu Glu Trp Lys Cys Met Tyr
    450                 455                 460
Ala Pro Lys Pro Lys Val Met Gln Thr Cys Asn Leu Phe Asp Cys Pro
465                 470                 475                 480
Lys Trp Ile Ala Met Glu Trp Ser Gln Cys Thr Val Thr Cys Gly Arg
                485                 490                 495
Gly Leu Arg Tyr Arg Val Val Leu Cys Ile Asn His Arg Gly Glu His
            500                 505                 510
Val Gly Gly Cys Asn Pro Gln Leu Lys Leu His Ile Lys Glu Glu Cys
        515                 520                 525
Val Ile Pro Ile Pro Cys Tyr Lys Pro Lys Glu Lys Ser Pro Val Glu
    530                 535                 540
Ala Lys Leu Pro Trp Leu Lys Gln Ala Gln Glu Leu Glu Glu Thr Arg
545                 550                 555                 560
Ile Ala Thr Glu Glu Pro Thr Phe Ile Pro Glu Pro Trp Ser Ala Cys
                565                 570                 575
```

```
Ser Thr Thr Cys Gly Pro Gly Val Gln Val Arg Glu Val Lys Cys Arg
        580                 585                 590
Val Leu Leu Thr Phe Thr Gln Thr Glu Thr Glu Leu Pro Glu Glu Glu
            595                 600                 605
Cys Glu Gly Pro Lys Leu Pro Thr Glu Arg Pro Cys Leu Leu Glu Ala
        610                 615                 620
Cys Asp Glu Ser Pro Ala Ser Arg Glu Leu Asp Ile Pro Leu Pro Glu
625                 630                 635                 640
Asp Ser Glu Thr Thr Tyr Asp Trp Glu Tyr Ala Gly Phe Thr Pro Cys
                645                 650                 655
Thr Ala Thr Cys Leu Gly Gly His Gln Glu Ala Ile Ala Val Cys Leu
            660                 665                 670
His Ile Gln Thr Gln Thr Val Asn Asp Ser Leu Cys Asp Met Val
        675                 680                 685
His Arg Pro Pro Ala Met Ser Gln Ala Cys Asn Thr Glu Pro Cys Pro
        690                 695                 700
Pro Arg Trp His Val Gly Ser Trp Gly Pro Cys Ser Ala Thr Cys Gly
705                 710                 715                 720
Val Gly Ile Gln Thr Arg Asp Val Tyr Cys Leu His Pro Gly Glu Thr
                725                 730                 735
Pro Ala Pro Pro Glu Glu Cys Arg Asp Glu Lys Pro His Ala Leu Gln
            740                 745                 750
Ala Cys Asn Gln Phe Asp Cys Pro Pro Gly Trp His Ile Glu Glu Trp
        755                 760                 765
Gln Gln Cys Ser Arg Thr Cys Gly Gly Thr Gln Asn Arg Arg Val
        770                 775                 780
Thr Cys Arg Gln Leu Leu Thr Asp Gly Ser Phe Leu Asn Leu Ser Asp
785                 790                 795                 800
Glu Leu Cys Gln Gly Pro Lys Ala Ser Ser His Lys Ser Cys Ala Arg
                805                 810                 815
Thr Asp Cys Pro Pro His Leu Ala Val Gly Asp Trp Ser Lys Glu His
            820                 825                 830
Ser Met Gln Glu Asp Asn Gly Ala Gly Ser Thr Gln Phe
        835                 840                 845

<210> SEQ ID NO 13
<211> LENGTH: 2316
<212> TYPE: DNA
<213> ORGANISM: homo sapiens

<400> SEQUENCE: 13
atggcttcct ggacgagccc ctggtgggtg ctgatagggga tggtcttcat gcactctccc    60
ctcccgcaga ccacagctga gaaatctcct ggaaggaatt gtgaagggca gaacattcgg   120
tacaagacat gcagcaatca tgactgccct ccagatgcag aagatttcag agcccagcag   180
tgctcagcct acaatgatgt ccagtatcag gggcattact atgaatggct ccacgatat   240 aatgatcctg ctgccccgtg tgcactcaag tgtcatgcac aaggacaaaa cttggtggtg   300
gagctggcac ctaaggtact ggatggaact cgttgcaaca cggactcctt ggacatgtgt   360
atcagtggca tctgtcaggc agtgggctgc gatcggcaac tgggaagcaa tgccaaggag   420
gacaactgtg gagtctgtgc cggcgatggc tccacctgca ggcttgtacg gggacaatca   480
aagtcacacg tttctcctga aaaagagaa gaaaatgtaa ttgctgttcc tttgggaagt   540
cgaagtgtga gaattacagt gaaaggacct gcccacctct ttattgaatc aaaaacactt   600
```

```
caaggaagca aaggagaaca cagctttaac agccccggcg tctttgtcgt agaaaacaca    660
acagtggaat tcagaggggc tccgagaggc aaacttttta agattccagg acctctgatg    720
gctgatttca tcttcaagac caggtacact gcagccaaag acagcgtggt tcagttcttc    780
ttttaccagc ccatcagtca tcagtggaga caaactgact tctttccctg cactgtgacg    840
tgtggaggag ttatcagct caattctgct gaatgtgtgg atatccgctt gaagagggta    900
gttcctgacc attattgtca ctactaccct gaaaatgtaa accaaaaccc aaaactgaag    960
gaatgcagca tggatccctg cccatcaagt gatggattta agagataat gcccctatgac   1020 cacttccaac ctcttcctcg ctgggaacat aatccttgga ctgcatgttc cgtgtcctgt   1080
ggaggaggga ttcagagacg gagctttgtg tgtgtagagg aatccatgca tggagagata   1140
ttgcaggtgg aagaatggaa gtgcatgtac gcacccaaac ccaaggttat gcaaacttgt   1200
aatctgtttg attgccccaa gtggattgcc atggagtggt ctcagtgcac agtgacttgt   1260
ggccgagggt tacggtaccg ggttgttctg tgtattaacc accgcggaga gcatgttggg   1320
ggctgcaatc cacaactgaa gttacacatc aaagaagaat gtgtcattcc catcccgtgt   1380
tataaaccaa agaaaaaag tccagtggaa gcaaaattgc cttggctgaa acaagcacaa   1440
gaactagaag agaccagaat agcaacagaa gaaccaacgt tcattccaga accctggtca   1500
gcctgcagta ccacgtgtgg gccaggtgtg caggtccgcg aggtgaagtg ccgtgtgctc   1560
ctcacattca cgcagactga gactgagctg cccgaggaag agtgtgaagg ccccaagctg   1620
cccaccgaac ggccctgcct cctggaagca tgtgatgaga gccggcctc ccgagagcta   1680 gacatccctc tccctgagga cagtgagacg acttacgact gggagtacgc tgggttcacc   1740
ccttgcacag caacatgctt ggggaggccat caagaagcca tagcagtgtg cttacatatc   1800
cagacccagc agacagtcaa tgacagcttg tgtgatatgg tccaccgtcc tccagccatg   1860
agccaggcct gtaacacaga gccctgtccc ccaggtggc atgtgggctc ttgggggccc   1920
tgctcagcta cctgtggagt tggaattcag acccgagatg tgtactgcct gcacccaggg   1980
gagacccctg cccctcctga ggagtgccga gatgaaaagc cccatgcttt acaagcatgc   2040
aatcagtttg actgccctcc tggctggcac attgaagaat ggcagcagtg ttccaggact   2100
tgtggcgggg gaactcagaa cagaagagtc acctgtcggc agctgctaac ggatggcagc   2160
tttttgaatc tctcagatga attgtgccaa ggacccaagg catcgtctca caagtcctgt   2220
gccaggacag actgtcctcc acattagct gtgggagact ggtcgaagga gcattcaatg   2280
caagaggaca atggagcagg atctacacaa ttctaa                             2316
```

<210> SEQ ID NO 14
<211> LENGTH: 771
<212> TYPE: PRT
<213> ORGANISM: homo sapiens

<400> SEQUENCE: 14

Met Ala Ser Trp Thr Ser Pro Trp Trp Val Leu Ile Gly Met Val Phe
1               5                   10                  15

Met His Ser Pro Leu Pro Gln Thr Thr Ala Glu Lys Ser Pro Gly Arg
            20                  25                  30

Asn Cys Glu Gly Gln Asn Ile Arg Tyr Lys Thr Cys Ser Asn His Asp
        35                  40                  45

Cys Pro Pro Asp Ala Glu Asp Phe Arg Ala Gln Cys Ser Ala Tyr
    50                  55                  60

Asn Asp Val Gln Tyr Gln Gly His Tyr Tyr Glu Trp Leu Pro Arg Tyr

-continued

```
          65                  70                  75                  80
Asn Asp Pro Ala Ala Pro Cys Ala Leu Lys Cys His Ala Gln Gly Gln
                85                  90                  95
Asn Leu Val Val Glu Leu Ala Pro Lys Val Leu Asp Gly Thr Arg Cys
               100                 105                 110
Asn Thr Asp Ser Leu Asp Met Cys Ile Ser Gly Ile Cys Gln Ala Val
               115                 120                 125
Gly Cys Asp Arg Gln Leu Gly Ser Asn Ala Lys Glu Asp Asn Cys Gly
               130                 135                 140
Val Cys Ala Gly Asp Gly Ser Thr Cys Arg Leu Val Arg Gly Gln Ser
145                150                 155                 160
Lys Ser His Val Ser Pro Glu Lys Arg Glu Glu Asn Val Ile Ala Val
               165                 170                 175
Pro Leu Gly Ser Arg Ser Val Arg Ile Thr Val Lys Gly Pro Ala His
               180                 185                 190
Leu Phe Ile Glu Ser Lys Thr Leu Gln Gly Ser Lys Gly Glu His Ser
               195                 200                 205
Phe Asn Ser Pro Gly Val Phe Val Glu Asn Thr Thr Val Glu Phe
210                215                 220
Gln Arg Gly Ser Glu Arg Gln Thr Phe Lys Ile Pro Gly Pro Leu Met
225                230                 235                 240
Ala Asp Phe Ile Phe Lys Thr Arg Tyr Thr Ala Ala Lys Asp Ser Val
               245                 250                 255
Val Gln Phe Phe Phe Tyr Gln Pro Ile Ser His Gln Trp Arg Gln Thr
               260                 265                 270
Asp Phe Phe Pro Cys Thr Val Thr Cys Gly Gly Gly Tyr Gln Leu Asn
               275                 280                 285
Ser Ala Glu Cys Val Asp Ile Arg Leu Lys Arg Val Val Pro Asp His
               290                 295                 300
Tyr Cys His Tyr Tyr Pro Glu Asn Val Lys Pro Lys Pro Lys Leu Lys
305                310                 315                 320
Glu Cys Ser Met Asp Pro Cys Pro Ser Ser Asp Gly Phe Lys Glu Ile
               325                 330                 335
Met Pro Tyr Asp His Phe Gln Pro Leu Pro Arg Trp Glu His Asn Pro
               340                 345                 350
Trp Thr Ala Cys Ser Val Ser Cys Gly Gly Gly Ile Gln Arg Arg Ser
               355                 360                 365
Phe Val Cys Val Glu Glu Ser Met His Gly Glu Ile Leu Gln Val Glu
370                375                 380
Glu Trp Lys Cys Met Tyr Ala Pro Lys Pro Lys Val Met Gln Thr Cys
385                390                 395                 400
Asn Leu Phe Asp Cys Pro Lys Trp Ile Ala Met Glu Trp Ser Gln Cys
               405                 410                 415
Thr Val Thr Cys Gly Arg Gly Leu Arg Tyr Arg Val Val Leu Cys Ile
               420                 425                 430
Asn His Arg Gly Glu His Val Gly Gly Cys Asn Pro Gln Leu Lys Leu
               435                 440                 445
His Ile Lys Glu Glu Cys Val Ile Pro Ile Pro Cys Tyr Lys Pro Lys
               450                 455                 460
Glu Lys Ser Pro Val Glu Ala Lys Leu Pro Trp Leu Lys Gln Ala Gln
465                470                 475                 480
Glu Leu Glu Glu Thr Arg Ile Ala Thr Glu Pro Thr Phe Ile Pro
               485                 490                 495
```

```
Glu Pro Trp Ser Ala Cys Ser Thr Thr Cys Gly Pro Gly Val Gln Val
                500                 505                 510

Arg Glu Val Lys Cys Arg Val Leu Leu Thr Phe Thr Gln Thr Glu Thr
            515                 520                 525

Glu Leu Pro Glu Glu Cys Glu Gly Pro Lys Leu Pro Thr Glu Arg
        530                 535                 540

Pro Cys Leu Leu Glu Ala Cys Asp Glu Ser Pro Ala Ser Arg Glu Leu
545                 550                 555                 560

Asp Ile Pro Leu Pro Glu Asp Ser Glu Thr Thr Tyr Asp Trp Glu Tyr
                565                 570                 575

Ala Gly Phe Thr Pro Cys Thr Ala Thr Cys Leu Gly Gly His Gln Glu
                580                 585                 590

Ala Ile Ala Val Cys Leu His Ile Gln Thr Gln Gln Thr Val Asn Asp
                595                 600                 605

Ser Leu Cys Asp Met Val His Arg Pro Pro Ala Met Ser Gln Ala Cys
                610                 615                 620

Asn Thr Glu Pro Cys Pro Pro Arg Trp His Val Gly Ser Trp Gly Pro
625                 630                 635                 640

Cys Ser Ala Thr Cys Gly Val Gly Ile Gln Thr Arg Asp Val Tyr Cys
                645                 650                 655

Leu His Pro Gly Glu Thr Pro Ala Pro Pro Glu Glu Cys Arg Asp Glu
                660                 665                 670

Lys Pro His Ala Leu Gln Ala Cys Asn Gln Phe Asp Cys Pro Pro Gly
                675                 680                 685

Trp His Ile Glu Glu Trp Gln Gln Cys Ser Arg Thr Cys Gly Gly Gly
                690                 695                 700

Thr Gln Asn Arg Arg Val Thr Cys Arg Gln Leu Leu Thr Asp Gly Ser
705                 710                 715                 720

Phe Leu Asn Leu Ser Asp Glu Leu Cys Gln Gly Pro Lys Ala Ser Ser
                725                 730                 735

His Lys Ser Cys Ala Arg Thr Asp Cys Pro Pro His Leu Ala Val Gly
                740                 745                 750

Asp Trp Ser Lys Glu His Ser Met Gln Glu Asp Asn Gly Ala Gly Ser
                755                 760                 765

Thr Gln Phe
    770

<210> SEQ ID NO 15
<211> LENGTH: 4854
<212> TYPE: DNA
<213> ORGANISM: homo sapiens

<400> SEQUENCE: 15
atggcttcct ggacgagccc ctggtgggtg ctgatagggg tggtcttcat gcactctccc     60
ctcccgcaga ccacagctga gaaatctcct ggaaggaatt gtgaagggca gaacattcgg    120
tacaagacat gcagcaatca tgactgccct ccagatgcag aagatttcag agcccagcag    180
tgctcagcct acaatgatgt ccagtatcag gggcattact atgaatggct tccacgatat    240
aatgatcctg ctgccccgtg tgcactcaag tgtcatgcac aaggacaaaa cttggtggtg    300
gagctggcac ctaaggtact ggatggaact cgttgcaaca cggactcctt ggacatgtgt    360
atcagtggca tctgtcaggc agtgggctgc gatcggcaac tggaagcaa tgccaaggag    420 gacaactgtg gagtctgtgc cggcgatggc tccacctgca ggcttgtacg gggacaatca    480
```

-continued

| | |
|---|---|
| aagtcacacg tttctcctga aaaagagaa gaaaatgtaa ttgctgttcc tttgggaagt | 540 |
| cgaagtgtga gaattacagt gaaaggacct gcccacctct ttattgaatc aaaaacactt | 600 |
| caaggaagca aaggagaaca cagctttaac agccccggcg tctttgtcgt agaaaacaca | 660 |
| acagtggaat tcagaggggg ctccgagagg caaacttttta agattccagg acctctgatg | 720 |
| gctgatttca tcttcaagac caggtacact gcagccaaag acagcgtggt tcagttcttc | 780 |
| ttttaccagc ccatcagtca tcagtggaga caaactgact tctttccctg cactgtgacg | 840 |
| tgtggaggag gttatcagct caattctgct gaatgtgtgg atatccgctt gaagagggta | 900 |
| gttcctgacc attattgtca ctactaccct gaaaatgtaa aaccaaaacc aaaactgaag | 960 |
| gaatgcagca tggatccctg cccatcaagt gatggattta agagataat gccctatgac | 1020 |
| cacttccaac ctcttcctcg ctgggaacat aatccttgga ctgcatgttc cgtgtcctgt | 1080 |
| ggaggaggga ttcagagacg gagctttgtg tgtgtagagg aatccatgca tggagagata | 1140 |
| ttgcaggtgg aagaatggaa gtgcatgtac gcacccaaac ccaaggttat gcaaacttgt | 1200 |
| aatctgtttg attgccccaa gtggattgcc atggagtggt ctcagtgcac agtgacttgt | 1260 |
| ggccgagggt tacggtaccg ggttgttctg tgtattaacc accgcggaga gcatgttggg | 1320 |
| ggctgcaatc cacaactgaa gttacacatc aaagaagaat gtgtcattcc catcccgtgt | 1380 |
| tataaaccaa aagaaaaag tccagtggaa gcaaaattgc cttggctgaa acaagcacaa | 1440 |
| gaactagaag agaccagaat agcaacagaa gaaccaacgt tcattccaga accctggtca | 1500 |
| gcctgcagta ccacgtgtgg gccaggtgtg caggtccgcg aggtgaagtg ccgtgtgctc | 1560 |
| ctcacattca cgcagactga gactgagctg cccgaggaag agtgtgaagg ccccaagctg | 1620 |
| cccaccgaac ggccctgcct cctggaagca tgtgatgaga gccggcctc ccgagagcta | 1680 |
| gacatccctc tccctgagga cagtgagacg acttacgact gggagtacgc tgggttcacc | 1740 |
| ccttgcacag caacatgctt gggaggccat caagaagcca tagcagtgtg cttacatatc | 1800 |
| cagacccagc agacagtcaa tgacagcttg tgtgatatgg tccaccgtcc tccagccatg | 1860 |
| agccaggcct gtaacacaga gccctgtccc ccaggtggc atgtgggctc ttgggggccc | 1920 |
| tgctcagcta cctgtggagt tggaattcag acccgagatg tgtactgcct gcacccaggg | 1980 |
| gagacccctg cccctcctga ggagtgccga gatgaaaagc cccatgcttt acaagcatgc | 2040 |
| aatcagtttg actgccctcc tggctggcac attgaagaat ggcagcagtg ttccaggact | 2100 |
| tgtggcgggg gaactcagaa cagaagagtc acctgtcggc agctgctaac ggatggcagc | 2160 |
| ttttttgaatc tctcagatga attgtgccaa ggacccaagg catcgtctca caagtcctgt | 2220 |
| gccaggacag actgtcctcc acatttagct gtgggagact ggtcgaagtg ttctgtcagt | 2280 |
| tgtggtgttg gaatccagag aagaaagcag gtgtgtcaaa ggctggcagc caaaggtcgg | 2340 |
| cgcatccccc tcagtgagat gatgtgcagg gatctaccag ggttccctct tgtaagatct | 2400 |
| tgccagatgc ctgagtgcag taaaatcaaa tcagagatga agacaaaact tggtgagcag | 2460 |
| ggtccgcaga tcctcagtgt ccagagagtc tacattcaga caagggaaga gaagcgtatt | 2520 |
| aacctgacca ttggtagcag agcctatttg ctgcccaaca catccgtgat tattaagtgc | 2580 |
| cccgtgcgac gattccagaa atctctgatc cagtgggaga aggatggccg ttgcctgcag | 2640 |
| aactccaaac ggcttggcat caccaagtca ggctcactaa aaatccacgg tcttgctgcc | 2700 |
| cccgacatcg gcgtgtaccg gtgcattgca ggctctgcac aggaaacagt tgtgctcaag | 2760 |
| ctcattggta ctgacaaccg gctcatcgca cgcccagccc tcaggagcc tatgagggaa | 2820 |
| tatcctggga tggaccacag cgaagccaat agtttgggag tcacatggca caaaatgagg | 2880 |

```
caaatgtgga ataacaaaaa tgacctttat ctggatgatg accacattag taaccagcct    2940
ttcttgagag ctctgttagg ccactgcagc aattctgcag gaagcaccaa ctcctgggag    3000
ttgaagaata agcagtttga agcagcagtt aaacaaggag catatagcat ggatacagcc    3060
cagtttgatg agctgataag aaacatgagt cagctcatgg aaaccggaga ggtcagcgat    3120
gatcttgcgt cccagctgat atatcagctg gtggccgaat tagccaaggc acagccaaca    3180
cacatgcagt ggcggggcat ccaggaagag acacctcctg ctgctcagct cagaggggaa    3240
acagggagtg tgtcccaaag ctcgcatgca aaaaactcag gcaagctgac attcaagccg    3300
aaaggacctg ttctcatgag gcaaagccaa cctccctcaa tttcatttaa taaaacaata    3360
aattccagga ttggaaatac agtatacatt acaaaaagga cagaggtcat caatatactg    3420
tgtgacctta ttaccccccag tgaggccaca tatacatgga ccaaggatgg aaccttgtta    3480
cagccctcag taaaaataat tttgatggga actgggaaga tacagataca gaatcctaca    3540
aggaaagaac aaggcatata tgaatgttct gtagctaatc atcttggttc agatgtggaa    3600
agttcttctg tgctgtatgc agaggcacct gtcatcttgt ctgttgaaag aaatatcacc    3660
aaaccagagc acaaccatct gtctgttgtg gttggaggca tcgtggaggc agcccttgga    3720
gcaaacgtga caatccgatg tcctgtaaaa ggtgtccctc agcctaatat aacttggttg    3780
aagagaggag gatctctgag tggcaatgtt tccttgcttt tcaatggatc cctgttgttg    3840
cagaatgttt cccttgaaaa tgaaggaacc tacgtctgca tagccaccaa tgctcttgga    3900
aaggcagtgg caacatctgt actccacttg ctggaacgaa gatggccaga gagtagaatc    3960
gtatttctgc aaggacataa aaagtacatt ctccaggcaa ccaacactag aaccaacagc    4020
aatgacccaa caggagaacc cccgcctcaa gagcctttt gggagcctgg taactggtca    4080
cattgttctg ccacctgtgg tcatttggga gcccgcattc agagacccca gtgtgtgatg    4140
gccaatgggc aggaagtgag tgaggccctg tgtgatcacc tccagaagcc actggctggg    4200
tttgagcccct gtaacatccg ggactgccca gcgaggtggt tcacaagtgt gtggtcacag    4260
tgctctgtgt cttgcggtga aggataccac agtcggcagg tgacgtgcaa gcggacaaaa    4320
gccaatggaa ctgtgcaggt ggtgtctcca agagcatgtg cccctaaaga ccggcctctg    4380
ggaagaaaac catgttttgg tcatccatgt gttcagtggg aaccagggaa ccggtgtcct    4440
ggacgttgca tggccgtgc tgtgaggatg cagcagcgtc acacagcttg tcaacacaac    4500
agctctgact ccaactgtga tgacagaaag agacccacct taagaaggaa ctgcacatca    4560
ggggcctgtg atgtgtgttg gcacacaggc ccttggaagc cctgtacagc agcctgtggc    4620
agggggtttcc agtctcggaa agtcgactgt atccacacaa ggagttgcaa acctgtggcc    4680
aagagacact gtgtacagaa aaagaaacca atttcctggc ggcactgtct tgggccctcc    4740
tgtgatagag actgcacaga cacaactcac tactgtatgt ttgtaaaaca tcttaatttg    4800
tgttctctag accgctacaa acaaaggtgc tgccagtcat gtcaagaggg ataa          4854
```

<210> SEQ ID NO 16  
<211> LENGTH: 1617  
<212> TYPE: PRT  
<213> ORGANISM: homo sapiens

<400> SEQUENCE: 16

Met Ala Ser Trp Thr Ser Pro Trp Trp Val Leu Ile Gly Met Val Phe  
 1               5                  10                  15

Met His Ser Pro Leu Pro Gln Thr Thr Ala Glu Lys Ser Pro Gly Arg

-continued

```
                 20                  25                  30
Asn Cys Glu Gly Gln Asn Ile Arg Tyr Lys Thr Cys Ser Asn His Asp
                 35                  40                  45
Cys Pro Pro Asp Ala Glu Asp Phe Arg Ala Gln Cys Ser Ala Tyr
 50                  55                  60
Asn Asp Val Gln Tyr Gln Gly His Tyr Tyr Glu Trp Leu Pro Arg Tyr
 65                  70                  75                  80
Asn Asp Pro Ala Ala Pro Cys Ala Leu Lys Cys His Ala Gln Gly Gln
                 85                  90                  95
Asn Leu Val Val Glu Leu Ala Pro Lys Val Leu Asp Gly Thr Arg Cys
                100                 105                 110
Asn Thr Asp Ser Leu Asp Met Cys Ile Ser Gly Ile Cys Gln Ala Val
                115                 120                 125
Gly Cys Asp Arg Gln Leu Gly Ser Asn Ala Lys Glu Asp Asn Cys Gly
            130                 135                 140
Val Cys Ala Gly Asp Gly Ser Thr Cys Arg Leu Val Arg Gly Gln Ser
145                 150                 155                 160
Lys Ser His Val Ser Pro Glu Lys Arg Glu Asn Val Ile Ala Val
                165                 170                 175
Pro Leu Gly Ser Arg Ser Val Arg Ile Thr Val Lys Gly Pro Ala His
            180                 185                 190
Leu Phe Ile Glu Ser Lys Thr Leu Gln Gly Ser Lys Gly Glu His Ser
            195                 200                 205
Phe Asn Ser Pro Gly Val Phe Val Val Glu Asn Thr Thr Val Glu Phe
            210                 215                 220
Gln Arg Gly Ser Glu Arg Gln Thr Phe Lys Ile Pro Gly Pro Leu Met
225                 230                 235                 240
Ala Asp Phe Ile Phe Lys Thr Arg Tyr Thr Ala Ala Lys Asp Ser Val
                245                 250                 255
Val Gln Phe Phe Phe Tyr Gln Pro Ile Ser His Gln Trp Arg Gln Thr
            260                 265                 270
Asp Phe Phe Pro Cys Thr Val Thr Cys Gly Gly Tyr Gln Leu Asn
            275                 280                 285
Ser Ala Glu Cys Val Asp Ile Arg Leu Lys Arg Val Val Pro Asp His
290                 295                 300
Tyr Cys His Tyr Tyr Pro Glu Asn Val Lys Pro Lys Pro Lys Leu Lys
305                 310                 315                 320
Glu Cys Ser Met Asp Pro Cys Pro Ser Ser Asp Gly Phe Lys Glu Ile
                325                 330                 335
Met Pro Tyr Asp His Phe Gln Pro Leu Pro Arg Trp Glu His Asn Pro
            340                 345                 350
Trp Thr Ala Cys Ser Val Ser Cys Gly Gly Gly Ile Gln Arg Arg Ser
            355                 360                 365
Phe Val Cys Val Glu Glu Ser Met His Gly Glu Ile Leu Gln Val Glu
            370                 375                 380
Glu Trp Lys Cys Met Tyr Ala Pro Lys Pro Lys Val Met Gln Thr Cys
385                 390                 395                 400
Asn Leu Phe Asp Cys Pro Lys Trp Ile Ala Met Glu Trp Ser Gln Cys
                405                 410                 415
Thr Val Thr Cys Gly Arg Gly Leu Arg Tyr Arg Val Val Leu Cys Ile
                420                 425                 430
Asn His Arg Gly Glu His Val Gly Gly Cys Asn Pro Gln Leu Lys Leu
            435                 440                 445
```

```
His Ile Lys Glu Glu Cys Val Ile Pro Ile Pro Cys Tyr Lys Pro Lys
    450                 455                 460
Glu Lys Ser Pro Val Glu Ala Lys Leu Pro Trp Leu Lys Gln Ala Gln
465                 470                 475                 480
Glu Leu Glu Glu Thr Arg Ile Ala Thr Glu Pro Thr Phe Ile Pro
                485                 490                 495
Glu Pro Trp Ser Ala Cys Ser Thr Thr Cys Gly Pro Gly Val Gln Val
            500                 505                 510
Arg Glu Val Lys Cys Arg Val Leu Leu Thr Phe Thr Gln Thr Glu Thr
            515                 520                 525
Glu Leu Pro Glu Glu Cys Glu Gly Pro Lys Leu Pro Thr Glu Arg
530                 535                 540
Pro Cys Leu Leu Glu Ala Cys Asp Glu Ser Pro Ala Ser Arg Glu Leu
545                 550                 555                 560
Asp Ile Pro Leu Pro Glu Asp Ser Glu Thr Thr Tyr Asp Trp Glu Tyr
                565                 570                 575
Ala Gly Phe Thr Pro Cys Thr Ala Thr Cys Leu Gly His Gln Glu
                580                 585                 590
Ala Ile Ala Val Cys Leu His Ile Gln Thr Gln Gln Thr Val Asn Asp
            595                 600                 605
Ser Leu Cys Asp Met Val His Arg Pro Pro Ala Met Ser Gln Ala Cys
            610                 615                 620
Asn Thr Glu Pro Cys Pro Pro Arg Trp His Val Gly Ser Trp Gly Pro
625                 630                 635                 640
Cys Ser Ala Thr Cys Gly Val Gly Ile Gln Thr Arg Asp Val Tyr Cys
                645                 650                 655
Leu His Pro Gly Glu Thr Pro Ala Pro Pro Glu Glu Cys Arg Asp Glu
                660                 665                 670
Lys Pro His Ala Leu Gln Ala Cys Asn Gln Phe Asp Cys Pro Pro Gly
            675                 680                 685
Trp His Ile Glu Glu Trp Gln Gln Cys Ser Arg Thr Cys Gly Gly Gly
            690                 695                 700
Thr Gln Asn Arg Arg Val Thr Cys Arg Gln Leu Leu Thr Asp Gly Ser
705                 710                 715                 720
Phe Leu Asn Leu Ser Asp Glu Leu Cys Gln Gly Pro Lys Ala Ser Ser
                725                 730                 735
His Lys Ser Cys Ala Arg Thr Asp Cys Pro Pro His Leu Ala Val Gly
            740                 745                 750
Asp Trp Ser Lys Cys Ser Val Ser Cys Gly Val Gly Ile Gln Arg Arg
            755                 760                 765
Lys Gln Val Cys Gln Arg Leu Ala Ala Lys Gly Arg Arg Ile Pro Leu
770                 775                 780
Ser Glu Met Met Cys Arg Asp Leu Pro Gly Phe Pro Leu Val Arg Ser
785                 790                 795                 800
Cys Gln Met Pro Glu Cys Ser Lys Ile Lys Ser Glu Met Lys Thr Lys
                805                 810                 815
Leu Gly Glu Gln Gly Pro Gln Ile Leu Ser Val Gln Arg Val Tyr Ile
                820                 825                 830
Gln Thr Arg Glu Glu Lys Arg Ile Asn Leu Thr Ile Gly Ser Arg Ala
            835                 840                 845
Tyr Leu Leu Pro Asn Thr Ser Val Ile Ile Lys Cys Pro Val Arg Arg
850                 855                 860
```

-continued

```
Phe Gln Lys Ser Leu Ile Gln Trp Glu Lys Asp Gly Arg Cys Leu Gln
865                 870                 875                 880

Asn Ser Lys Arg Leu Gly Ile Thr Lys Ser Gly Ser Leu Lys Ile His
            885                 890                 895

Gly Leu Ala Ala Pro Asp Ile Gly Val Tyr Arg Cys Ile Ala Gly Ser
                900                 905                 910

Ala Gln Glu Thr Val Val Leu Lys Leu Ile Gly Thr Asp Asn Arg Leu
        915                 920                 925

Ile Ala Arg Pro Ala Leu Arg Glu Pro Met Arg Glu Tyr Pro Gly Met
930                 935                 940

Asp His Ser Glu Ala Asn Ser Leu Gly Val Thr Trp His Lys Met Arg
945                 950                 955                 960

Gln Met Trp Asn Asn Lys Asn Asp Leu Tyr Leu Asp Asp His Ile
                965                 970                 975

Ser Asn Gln Pro Phe Leu Arg Ala Leu Leu Gly His Cys Ser Asn Ser
            980                 985                 990

Ala Gly Ser Thr Asn Ser Trp Glu Leu Lys Asn Lys Gln Phe Glu Ala
        995                 1000                1005

Ala Val Lys Gln Gly Ala Tyr Ser Met Asp Thr Ala Gln Phe Asp Glu
    1010                1015                1020

Leu Ile Arg Asn Met Ser Gln Leu Met Glu Thr Gly Glu Val Ser Asp
1025                1030                1035                1040

Asp Leu Ala Ser Gln Leu Ile Tyr Gln Leu Val Ala Glu Leu Ala Lys
                1045                1050                1055

Ala Gln Pro Thr His Met Gln Trp Arg Gly Ile Gln Glu Glu Thr Pro
            1060                1065                1070

Pro Ala Ala Gln Leu Arg Gly Glu Thr Gly Ser Val Ser Gln Ser Ser
        1075                1080                1085

His Ala Lys Asn Ser Gly Lys Leu Thr Phe Lys Pro Lys Gly Pro Val
    1090                1095                1100

Leu Met Arg Gln Ser Gln Pro Pro Ser Ile Ser Phe Asn Lys Thr Ile
1105                1110                1115                1120

Asn Ser Arg Ile Gly Asn Thr Val Tyr Ile Thr Lys Arg Thr Glu Val
                1125                1130                1135

Ile Asn Ile Leu Cys Asp Leu Ile Thr Pro Ser Glu Ala Thr Tyr Thr
            1140                1145                1150

Trp Thr Lys Asp Gly Thr Leu Leu Gln Pro Ser Val Lys Ile Ile Leu
        1155                1160                1165

Asp Gly Thr Gly Lys Ile Gln Ile Gln Asn Pro Thr Arg Lys Glu Gln
    1170                1175                1180

Gly Ile Tyr Glu Cys Ser Val Ala Asn His Leu Gly Ser Asp Val Glu
1185                1190                1195                1200

Ser Ser Ser Val Leu Tyr Ala Glu Ala Pro Val Ile Leu Ser Val Glu
                1205                1210                1215

Arg Asn Ile Thr Lys Pro Glu His Asn His Leu Ser Val Val Val Gly
            1220                1225                1230

Gly Ile Val Glu Ala Ala Leu Gly Ala Asn Val Thr Ile Arg Cys Pro
        1235                1240                1245

Val Lys Gly Val Pro Gln Pro Asn Ile Thr Trp Leu Lys Arg Gly Gly
    1250                1255                1260

Ser Leu Ser Gly Asn Val Ser Leu Leu Phe Asn Gly Ser Leu Leu Leu
1265                1270                1275                1280

Gln Asn Val Ser Leu Glu Asn Glu Gly Thr Tyr Val Cys Ile Ala Thr
```

```
                    1285            1290            1295
Asn Ala Leu Gly Lys Ala Val Ala Thr Ser Val Leu His Leu Leu Glu
                1300            1305            1310
Arg Arg Trp Pro Glu Ser Arg Ile Val Phe Leu Gln Gly His Lys Lys
            1315            1320            1325
Tyr Ile Leu Gln Ala Thr Asn Thr Arg Thr Asn Ser Asn Asp Pro Thr
        1330            1335            1340
Gly Glu Pro Pro Pro Gln Glu Pro Phe Trp Glu Pro Gly Asn Trp Ser
1345            1350            1355            1360
His Cys Ser Ala Thr Cys Gly His Leu Gly Ala Arg Ile Gln Arg Pro
                1365            1370            1375
Gln Cys Val Met Ala Asn Gly Gln Glu Val Ser Glu Ala Leu Cys Asp
            1380            1385            1390
His Leu Gln Lys Pro Leu Ala Gly Phe Glu Pro Cys Asn Ile Arg Asp
        1395            1400            1405
Cys Pro Ala Arg Trp Phe Thr Ser Val Trp Ser Gln Cys Ser Val Ser
    1410            1415            1420
Cys Gly Glu Gly Tyr His Ser Arg Gln Val Thr Cys Lys Arg Thr Lys
1425            1430            1435            1440
Ala Asn Gly Thr Val Gln Val Val Ser Pro Arg Ala Cys Ala Pro Lys
                1445            1450            1455
Asp Arg Pro Leu Gly Arg Lys Pro Cys Phe Gly His Pro Cys Val Gln
            1460            1465            1470
Trp Glu Pro Gly Asn Arg Cys Pro Gly Arg Cys Met Gly Arg Ala Val
        1475            1480            1485
Arg Met Gln Gln Arg His Thr Ala Cys Gln His Asn Ser Ser Asp Ser
    1490            1495            1500
Asn Cys Asp Asp Arg Lys Arg Pro Thr Leu Arg Arg Asn Cys Thr Ser
1505            1510            1515            1520
Gly Ala Cys Asp Val Cys Trp His Thr Gly Pro Trp Lys Pro Cys Thr
                1525            1530            1535
Ala Ala Cys Gly Arg Gly Phe Gln Ser Arg Lys Val Asp Cys Ile His
            1540            1545            1550
Thr Arg Ser Cys Lys Pro Val Ala Lys Arg His Cys Val Gln Lys Lys
        1555            1560            1565
Lys Pro Ile Ser Trp Arg His Cys Leu Gly Pro Ser Cys Asp Arg Asp
    1570            1575            1580
Cys Thr Asp Thr Thr His Tyr Cys Met Phe Val Lys His Leu Asn Leu
1585            1590            1595            1600
Cys Ser Leu Asp Arg Tyr Lys Gln Arg Cys Cys Gln Ser Cys Gln Glu
                1605            1610            1615
Gly
```

<210> SEQ ID NO 17
<211> LENGTH: 8578
<212> TYPE: DNA
<213> ORGANISM: homo sapiens

<400> SEQUENCE: 17
cgggctggag gccggcgtcg gggaaggtcc tggtgccgga ttccgcacga ggtgttgacg    60
ggcggcttct gccaacttct ccccagcgcg cgccgagccc gcgcggcccc ggggctgcac   120
gtcccagata cttctgcggc gcaaggctac aactgagacc cggaggagac tagacccat   180 ggcttcctgg acgagcccct ggtgggtgct gatagggatg gtcttcatgc actctcccct   240

```
cccgcagacc acagctgaga aatctcctgg agcctatttc cttcccgagt ttgcactttc    300
tcctcaggga gtttctgg aagacacaac aggggagcag ttcctcactt atcgctatga      360
tgaccagacc tcaagaaaca ctcgttcaga tgaagacaaa gatggcaact gggatgcttg    420
gggcgactgg agtgactgct cccggacctg tggggagga gcatcatatt ctctgcggag    480
atgtttgact ggaaggaatt gtgaagggca gaacattcgg tacaagacat gcagcaatca    540
tgactgccct ccagatgcag aagatttcag agcccagcag tgctcagcct acaatgatgt    600
ccagtatcag gggcattact atgaatggct ccacgatat aatgatcctg ctgccccgtg     660
tgcactcaag tgtcatgcac aaggacaaaa cttggtggtg gagctggcac ctaaggtact    720
ggatggaact cgttgcaaca cggactcctt ggacatgtgt atcagtggca tctgtcaggc    780
agtgggctgc gatcggcaac tgggaagcaa tgccaaggag acaactgtg gagtctgtgc     840
cggcgatggc tccacctgca ggcttgtacg gggacaatca aagtcacacg tttctcctga    900
aaaagagaa gaaaatgtaa ttgctgttcc tttgggaagt cgaagtgtga gaattacagt     960
gaaaggacct gcccacctct ttattgaatc aaaaacactt caaggaagca aggagaaca   1020
cagctttaac agccccggcg tctttgtcgt agaaaacaca acagtggaat tcagagggg    1080
ctccgagagg caaactttta agattccagg acctctgatg gctgatttca tcttcaagac   1140
caggtacact gcagccaaag acagcgtggt tcagttcttc ttttaccagc ccatcagtca   1200
tcagtggaga caaactgact tctttccctg cactgtgacg tgtggaggag ttatcagct    1260
caattctgct gaatgtgtgg atatccgctt gaagagggta gttcctgacc attattgtca   1320
ctactaccct gaaaatgtaa aaccaaaacc aaaactgaag gaatgcagca tggatccctg   1380
cccatcaagt gatggattta agagataat gccctatgac cacttccaac ctcttcctcg   1440
agctgggaac ataatccttg gactgcatgt tccgtgtcct gtggaggagg gattcagaga   1500
cggagctttg tgtgtgtaga ggaatccatg catggagaga tattgcaggt ggaagaatgg   1560
aagtgcatgt acgcacccaa acccaaggtt atgcaaactt gtaatctgtt tgattgcccc   1620
aagtggattg ccatggagtg gtctcagtgc acagtgactt gtggccgagg gttacggtac   1680
cgggttgttc tgtgtattaa ccaccgcgga gagcatgttg ggggctgcaa tccacaactg   1740
aagttacaca tcaaagaaga atgtgtcatt cccatcccgt gttataaacc aaaagaaaaa   1800
agtccagtgg aagcaaaatt gccttggctg aaacaagcac aagaactaga agagaccaga   1860
atagcaacag aagaaccaac gttcattcca gaaccctggt cagcctgcag taccacgtgt   1920
gggccaggtg tgcaggtccg cgaggtgaag tgccgtgtgc tcctcacatt cacgcagact   1980
gagactgagc tgcccgagga agagtgtgaa ggccccaagc tgcccaccga acggccctgc   2040
ctcctggaag catgtgatga gagcccggcc tcccgagagc tagacatccc tctccctgag   2100
gacagtgaga cgacttacga ctgggagtac gctgggttca ccccttgcac agcaacatgc   2160
ttgggaggcc atcaagaagc catagcagtg tgcttacata tccagaccca gcagacagtc   2220
aatgacagct tgtgtgatat ggtccaccgt cctccagcca tgagccaggc ctgtaacaca   2280
gagccctgtc cccccaggag agagccagca gcttgtagaa gcatgccggg ttacataatg   2340
gtcctgctag tctgaggaga gccttcttct ctaacaggat tcaacactgc tagggaagaa   2400
aggaggaaag caagaggcaa tagtgatgtg tttctgtacc agcttgttac ctatttcttg   2460
atataaaaaa caattctttta ttgagttcat tgtctgtgaa taagaaattg ttgcccattt   2520
cttaaataaa aacagctcca tctccaaaaa aaaaaaaaaa aaatggcatg tgggctcttg   2580
```

```
ggggccctgc tcagctacct gtggagttgg aattcagacc cgagatgtgt actgcctgca    2640
cccaggggag acccctgccc ctcctgagga gtgccgagat gaaaagcccc atgctttaca    2700
agcatgcaat cagtttgact gccctcctgg ctggcacatt gaagaatggc agcagtgttc    2760
caggacttgt ggcgggggaa ctcagaacag aagagtcacc tgtcggcagc tgctaacgga    2820
tggcagcttt ttgaatctct cagatgaatt gtgccaagga cccaaggcat cgtctcacaa    2880
gtcctgtgcc aggacagact gtcctccaca tttagctgtg ggagactggt cgaaggagca    2940
ttcaatgcaa gaggacaatg gagcaggatc tacacaattc taaagaaaag caagcatgac    3000
tcaaggattt cctcttcatc ctgtgttctt catgtagaga gacagcagag aggcagtcag    3060
agaatactgt ctgataagcc cttgaaaaag ctgtagggcc aagatgagat acagagatga    3120
ctcaaaacag agaatccagg aatgcataga tcctggtaaa aaggtgggga gatgagtaat    3180
aaattcattt gtgtaggatt aagactaatc aactaacaat tatattatag aacataacat    3240
aaatatcaga aatcttgaca ttatctaaat aataaaatga aaactaattg agatttggag    3300
agatgaggta gatgatatag tttggctgtg tccccaccca aatctcatct tgaattgtag    3360
ttcccataat tcccatgtgt tgtgggaggg actcagttgg agataattga atcatggggg    3420
cagtttccct catactgttc tcgtggtggt aaatgagtct cacgagatct gatggtttta    3480
taagggtttt ccttttcgc ttggctctca ttctctcttg cctgctgcca tgtaagacgt    3540 cccctttgccc ttcctttgtc ttctgccatg attgtgaggc ttccctagcc acgtggaact    3600
gagtctatta aacctctttc ctttataact tacccagtct tgggtatgtc tttattaaca    3660
acataagatt ggactaatac agtagaggaa atgtaagtgt gcttatttcc tcatccttct    3720
tagtagcaag tcaataaata ctctcctaag tcaaattgtc attaaaaata actatccaaa    3780
tctcttgttg gtttatttaa tcttctttat taactttaga gtgttctttc gggaattaat    3840
catggtttaa aaaatatcaa acattcaaca actctaattt tactttaatg tctttttttc    3900
taatatatct aataaaattg cattaaattt ttaagttgaa aaaaaaaaa aaaaaaaat    3960 gttctgtcag ttgtggtgtt ggaatccaga gaagaaagca ggtgtgtcaa aggctggcag    4020
ccaaaggtcg gcgcatcccc ctcagtgaga tgatgtgcag ggatctacca gggttccctc    4080
ttgtaagatc ttgccagatg cctgagtgca gtaaaatcaa atcagagatg aagacaaaac    4140
ttggtgagca gggtccgcag atcctcagtg tccagagagt ctacattcag acaagggaag    4200
agaagcgtat taacctgacc attggtagca gagcctattt gctgcccaac acatccgtga    4260
ttattaagtg ccccgtgcga cgattccaga aatctctgat ccagtgggag aaggatggcc    4320
gttgcctgca gaactccaaa cggcttggca tcaccaagtc aggctcacta aaaatccacg    4380
gtcttgctgc ccccgacatc ggcgtgtacc ggtgcattgc aggctctgca caggaaacag    4440
ttgtgctcaa gctcattggt actgacaacc ggctcatcgc acgcccagcc tcagggagc    4500 ctatgaggga atatcctggg atggaccaca gcgaagccaa tagtttggga gtcacatggc    4560
acaaaatgag gcaaatgtgg aataacaaaa atgacccttta tctggatgat gaccacatta    4620
gtaaccagcc tttcttgaga gctctgttag gccactgcag caattctgca ggaagcacca    4680
actcctggga gttgaagaat aagcagtttg aagcagcagt taaacaagga gcatatagca    4740
tggatacagc ccagtttgat gagctgataa gaaacatgag tcagctcatg gaaaccggag    4800
aggtcagcga tgatcttgcg tcccagctga tatatcagct ggtggccgaa ttagccaagg    4860
cacagccaac acacatgcag tggcgggca tccaggaaga gacacctcct gctgctcagc    4920 tcagaggga aacagggagt gtgtcccaaa gctcgcatgc aaaaaactca ggcaagctga    4980
```

-continued

```
cattcaagcc gaaaggacct gttctcatga ggcaaagcca acctccctca atttcattta    5040
ataaaacaat aaattccagg attggaaata cagtatacat tacaaaaagg acagaggtca    5100
tcaatatact gtgtgacctt attaccccca gtgaggccac atatacatgg accaaggatg    5160
gaaccttgtt acagccctca gtaaaaataa ttttggatgg aactgggaag atacagatac    5220
agaatcctac aaggaaagaa caaggcatat atgaatgttc tgtagctaat catcttggtt    5280
cagatgtgga aagttcttct gtgctgtatg cagaggcacc tgtcatcttg tctgttgaaa    5340
gaaatatcac caaaccagag cacaaccatc tgtctgttgt ggttggaggc atcgtggagg    5400
cagcccttgg agcaaacgtg acaatccgat gtcctgtaaa aggtgtccct cagcctaata    5460
taacttggtt gaagagagga ggatctctga gtggcaatgt ttccttgctt ttcaatggat    5520
ccctgttgtt gcagaatgtt tcccttgaaa atgaaggaac ctacgtctgc atagccacca    5580
atgctcttgg aaaggcagtg gcaacatctg tactccactt gctggaacga agatggccag    5640
agagtagaat cgtatttctg caaggacata aaaagtacat tctccaggca accaacacta    5700
gaaccaacag caatgaccca acaggagaac ccccgcctca agagccttttt gggagcctg    5760 gtaactggtc acattgttct gccacctgtg gtcatttggg agcccgcatt cagagacccc    5820
agtgtgtgat ggccaatggg caggaagtga gtgaggccct gtgtgatcac ctccagaagc    5880
cactggctgg gtttgagccc tgtaacatcc gggactgccc agcgaggtgg ttcacaagtg    5940
tgtggtcaca gtgctctgtg tcttgcggtg aaggatacca cagtcggcag gtgacgtgca    6000
agcggacaaa agccaatgga actgtgcagg tggtgtctcc aagagcatgt gcccctaaag    6060
accggcctct gggaagaaaa ccatgttttg gtcatccatg tgttcagtgg gaaccaggga    6120
accggtgtcc tggacgttgc atgggccgtg ctgtgaggat gcagcagcgt cacacagctt    6180
gtcaacacaa cagctctgac tccaactgtg atgacagaaa gagacccacc ttaagaagga    6240
actgcacatc agggggcctgt gatgtgtgtt ggcacacagg cccttggaag ccctgtacag    6300
cagcctgtgg caggggtttc cagtctcgga agtcgactg tatccacaca aggagttgca    6360
aacctgtggc caagagacac tgtgtacaga aaaagaaacc aatttcctgg cggcactgtc    6420
ttgggccctc ctgtgataga gactgcacag acacaactca ctactgtatg tttgtaaaac    6480
atcttaattt gtgttctcta gaccgctaca acaaaggtg ctgccagtca tgtcaagagg    6540
gataaacctt tggaggggtc atgatgctgc tgtgaagata aagtagaat ataaaagctc    6600 ttttcccat gtcgctgatt caaaaacatg tatttcttaa aagactagat tctatggatc    6660
aaacagaggt tgatgcaaaa acaccactgt taaggtgtaa agtgaaattt tccaatggta    6720 gtttatatt ccaattttttt aaaatgatgt attcaaggat gaacaaaata ctatagcatg    6780
catgccactg cacttgggac ctcatcatgt cagttgaatc gagaaatcac caagattatg    6840
agtgcatcct cacgtgctgc ctctttcctg tgatatgtag actagcacag agtggtacat    6900
cctaaaaact tgggaaacac agcaacccat gacttcctct tctctcaagt tgcaggtttt    6960
caacagtttt ataggtatt tgcattttag aagctctggc cagtagttgt taagatgttg    7020
gcattaatgg catttttcata gatccttggt ttagtctgtg aaaaagaaac catctctctg    7080
gataggctgt cacactgact gacctaaggg ttcatggaag catggcatct tgtccttgct    7140
tttagaacac ccatggaaga aaacacagag tagatattgc tgtcatttat acaactacag    7200
aaatttatct atgacctaat gaggcatctc ggaagtcaaa gaagagggaa agttaacctt    7260
ttctactgat ttcgtagtat attcagagct ttctttaag agctgtgaat gaaactttttt    7320
```

-continued

| | | | | |
|---|---|---|---|---|
| ctaagcacta | ttctattgca | cacaaacaga | aaaccaaagc | cttattagac ctaatttatg | 7380 |
| cataaagtag | tattcctgag | aactttattt | tggaaaattt | ataagaaagt aatccaaata | 7440 |
| agaaacacga | tagttgaaaa | taatttttat | agtaaataat | tgttttgggc tgattttca | 7500 |
| gtaaatccaa | agtgacttag | gttagaagtt | acactaagga | ccaggggttg gaatcagaat | 7560 |
| ttagtttaag | atttgaggaa | aagggtaagg | gttagtttca | gttttaggat tagagctaga | 7620 |
| attgggttag | gtgagaaaga | aagttaaggt | taaggctaga | gttgtcttta agggttaggg | 7680 |
| ttaggaccag | gttaggtcag | ggttggattg | gtttagatt | ggggccagtg ctggtgttag | 7740 |
| tgatagtgtc | aggatggagg | ttaggtttgg | agtaagcgtt | gttgctgaag tgagttcagg | 7800 |
| ctagcattaa | attgtaagtt | ctgaagctga | tttggttatg | gggtctttcc cctgtatact | 7860 |
| accagttgtg | tctttagatg | gcacacaagt | ccaaataagt | ggtcatactt ctttattcag | 7920 |
| ggtctcagct | gcctgtacac | ctgctgccta | catcttcttg | gcaacaaagt tacctgccac | 7980 |
| aggctctgct | gagcctagtt | cctggtcagt | aataactgaa | cagtgcattt tggctttgga | 8040 |
| tgtgtctgtg | gacaagcttg | ctgagtttct | ctaccatatt | ctgagcacac ggtctctttt | 8100 |
| gttctaattt | cagcttcact | gacactgggt | tgagcactac | tgtatgtgga gggtttggtg | 8160 |
| attgggaatg | gatggggac | agtgaggagg | acacaccagc | ccattagttg ttaatcatca | 8220 |
| atcacatctg | attgttgaag | gttattaaat | taaaagaaag | atcatttgta acatactctt | 8280 |
| tgtatatatt | tattatatga | aaggtgcaat | attttatttt | gtacagtatg taataaagac | 8340 |
| atgggacata | tatttttctt | attaacaaaa | tttcatatta | aattgcttca ctttgtattt | 8400 |
| aaagttaaaa | gttactattt | ttcatttgct | attgtacttt | cattgttgtc attcaattga | 8460 |
| cattcctgtg | tactgtattt | tactactgtt | tttataacat | gagagttaat gtttctgttt | 8520 |
| catgatcctt | atgtaattca | gaaataaatt | tactttgatt | attcagtggc atccttat | 8578 |